(12) United States Patent
Yan et al.

(10) Patent No.: US 8,541,568 B2
(45) Date of Patent: Sep. 24, 2013

(54) COMPOSITIONS AND METHODS USING SIRNA MOLECULES FOR TREATMENT OF GLIOMAS

(76) Inventors: Hai Yan, Durham, NC (US); Patrick Y. Lu, Rockville, MD (US); Darell D. Bigner, Durham, NC (US)

( * ) Notice: Subject to any disclaimer, the term of this patent is extended or adjusted under 35 U.S.C. 154(b) by 0 days.

(21) Appl. No.: 12/994,738

(22) PCT Filed: May 26, 2009

(86) PCT No.: PCT/US2009/003196
§ 371 (c)(1),
(2), (4) Date: Mar. 16, 2011

(87) PCT Pub. No.: WO2009/151539
PCT Pub. Date: Dec. 17, 2009

(65) Prior Publication Data
US 2011/0165227 A1    Jul. 7, 2011

Related U.S. Application Data

(60) Provisional application No. 61/055,966, filed on May 24, 2008.

(51) Int. Cl.
C07H 21/04 (2006.01)
C07H 21/02 (2006.01)
A61K 48/00 (2006.01)
C07K 5/00 (2006.01)

(52) U.S. Cl.
USPC ............ 536/24.5; 536/23.1; 514/44; 530/300

(58) Field of Classification Search
None
See application file for complete search history.

(56) References Cited

U.S. PATENT DOCUMENTS

| | | |
|---|---|---|
| 2005/0176024 A1 | 8/2005 | McSwiggen et al. |
| 2006/0121514 A1 | 6/2006 | Young et al. |
| 2006/0134787 A1 | 6/2006 | Zamore et al. |
| 2006/0265765 A1 | 11/2006 | Agatsuma et al. |
| 2007/0003519 A1 | 1/2007 | Lu et al. |
| 2008/0241198 A1 | 10/2008 | Liu et al. |
| 2008/0279920 A1 | 11/2008 | Tang et al. |
| 2010/0319074 A1 | 12/2010 | Lu et al. |
| 2012/0071540 A1 | 3/2012 | Lu et al. |

FOREIGN PATENT DOCUMENTS

| | | |
|---|---|---|
| WO | WO 0147496 A1 | 7/2001 |
| WO | WO 03040399 A2 | 5/2003 |
| WO | WO 03070918 A2 | 8/2003 |
| WO | WO 03090719 A1 | 11/2003 |
| WO | WO 2005076999 A2 | 8/2005 |
| WO | WO 2007079224 A2 | 7/2007 |

OTHER PUBLICATIONS de Wolf et al. (International Journal of Pharmaceutics, 331, 2007, pp. 167-175).*
Leng et al. (The Journal of Gene Medicine, 2005, 7, pp. 977-986).*
Michels et al. (Expert Opin. Investig. Drugs, 2006, 15(7), pp. 779-793).*
Kumar et al., "Transvascular delivery of small interfering RNA to the central nervous system," Nature, doi:10.1038/nature05901,17 Jun. 2007.
International Search Report and Written Opinion of the International Searching Authority of WIPO on International App. No. PCT/US2009/003196 (WO 2009/151539) of Sirnaomics, Inc., Oct. 5, 2009.
Cheema, Sangeeta, et al., "Regulation and Guidance of Cell Behavior for Tissue Regeneration Via the Sirna Mechanism", Wound Repair and Regeneration, vol. 15, No. 3, 2007, pp. 286-295.
Pickering, Lulu, "Progress in RNA-based therapeutics," Spectrum Drug Discovery and Design, Decision Resources, Inc., Waltham, Massachusetts, Aug. 4, 2005, pp. 6-1 to 6-20.
Whitmore, Mark, et al., "Synergistic Activation of Innate Immunity by Double-Stranded RNA and CpG DNA Promotes Enhanced Antitumor Activity," Cancer Research 64, 5850-5860, Aug. 15, 2004.

* cited by examiner

*Primary Examiner* — Amy Bowman
(74) *Attorney, Agent, or Firm* — Geoffrey M. Karny

(57) ABSTRACT

The present invention provides small interfering RNA (siRNA) molecules, compositions containing the molecules, and methods of using the compositions to treat gliomas.

16 Claims, 13 Drawing Sheets

SEQUENCE LISTING

```
<160> NUMBER OF SEQ ID NOS: 256

<210> SEQ ID NO 1
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
cacaacaaau gugaaugcag accaa                                              25

<210> SEQ ID NO 2
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
uuggucugca uucacauuug uugug                                              25
```

```
<210> SEQ ID NO 3
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 3
ucgagacccu gguggacaut t                                              21

<210> SEQ ID NO 4
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 4
auguccacca gggucucgat t                                              21

<210> SEQ ID NO 5
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
gccugcugcu ccucggcugc ggaua                                          25

<210> SEQ ID NO 6
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
ggucuggugc cuggucugau gaugu                                          25

<210> SEQ ID NO 7
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
cccaagggcu accaugccaa cuucu                                          25

<210> SEQ ID NO 8
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 8
agaaguuggc augguagccc uuggg                                        25

<210> SEQ ID NO 9
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
acaucaucag accaggcacc agacc                                        25

<210> SEQ ID NO 10
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
cuguagacac acccacccac auaca                                        25

<210> SEQ ID NO 11
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
uguauguggg uggguguguc uacag                                        25

<210> SEQ ID NO 12
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
cccuggugga caucuuccag gagua                                        25

<210> SEQ ID NO 13
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
uacuccugga agauguccac caggg                                        25

<210> SEQ ID NO 14
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14

```
ccaucgaugu cuacaugauc auggu                                               25

<210> SEQ ID NO 15
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
accaugauca uguagacauc gaugg                                               25

<210> SEQ ID NO 16
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
gaucaugguc aagugcugga ugaua                                               25

<210> SEQ ID NO 17
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
uaucauccag cacuugacca ugauc                                               25

<210> SEQ ID NO 18
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
gcugaagguu gugaaauucg gagaa                                               25

<210> SEQ ID NO 19
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
uucuccgaau uucacaaccu ucagc                                               25

<210> SEQ ID NO 20
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
gcugcugaag guugugaaau ucgga                                               25
```

```
<210> SEQ ID NO 21
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
uccgaauuuc acaaccuuca gcagc                                              25

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ala Cys Arg Gly Asp Met Phe Gly Cys Ala
1               5                   10

<210> SEQ ID NO 23
<211> LENGTH: 29
<212> TYPE: PRT
<213> ORGANISM: Rabies virus

<400> SEQUENCE: 23

Tyr Thr Ile Trp Met Pro Glu Asn Pro Arg Pro Gly Thr Pro Cys Asp
1               5                   10                  15

Ile Phe Thr Asn Ser Arg Gly Lys Arg Ala Ser Asn Gly
            20                  25

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Glu Asp Tyr Glu Leu Met Asp Leu Leu Ala Tyr Leu
1               5                   10

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gtgtgcgcag acagtgctcc a                                                  21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
ccaccatgcc aagtggtccc a                                                  21
```

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
cctggtggac atcttccagg a                                           21

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gcacatagga gagatgagct t                                           21

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
caagatccgc agacgtgtaa a                                           21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ggcgaggcag cttgagttaa a                                           21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
cttgagttaa acgaacgtac t                                           21

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ggaaggagcc tccctcaggg t                                           21

-continued

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
cactttgggt ccggagggcg a                                             21

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
cagtattctt ggttaatatt t                                             21

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gcctccgaaa ccatgaactt tct                                           23

<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
ctccaccatg ccaagtggtc cca                                           23

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
cctggtggac atcttccagg agt                                           23

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
cagcacatag gagagatgag ctt                                           23

<210> SEQ ID NO 39
<211> LENGTH: 23

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gcttgagtta aacgaacgta ctt                                          23

<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gttaaacgaa cgtacttgca gat                                          23

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ggaaggagcc tccctcaggg ttt                                          23

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
ctccctcagg gtttcgggaa cca                                          23

<210> SEQ ID NO 43
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
ctaatgttat tggtgtcttc act                                          23

<210> SEQ ID NO 44
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
gagaaagtgt tttatatacg gta                                          23

<210> SEQ ID NO 45
<211> LENGTH: 25
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 45
cctccgaaac catgaacttt ctgct                                          25

<210> SEQ ID NO 46
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
ccaccatgcc aagtggtccc aggct                                          25

<210> SEQ ID NO 47
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
ccctggtgga catcttccag gagta                                          25

<210> SEQ ID NO 48
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
gatccgcaga cgtgtaaatg ttcct                                          25

<210> SEQ ID NO 49
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
cgcagacgtg taaatgttcc tgcaa                                          25

<210> SEQ ID NO 50
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
gtaaatgttc ctgcaaaaac acaga                                          25

<210> SEQ ID NO 51
<211> LENGTH: 25
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 51
cagcttgagt taaacgaacg tactt                                       25

<210> SEQ ID NO 52
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
gttaaacgaa cgtacttgca gatgt                                       25

<210> SEQ ID NO 53
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
ccatgccaag tggtcccagg ctgca                                       25

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
ccctgactac cagcaggact t                                           21

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
ctgactacca gcaggacttc t                                           21

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56 caggggatg aaagaatgca t                                            21

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 57
gggggatgaa agaatgcatt t                                              21

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
gaattctcca aaatggcccg a                                              21

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
ccatcgatgt ctacatgatc a                                              21

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
gatcatggtc aagtgctgga t                                              21

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
cgatgtctac atgatcatgg t                                              21

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
caaagtgcct atcaagtgga t                                              21

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
```
ctggatccca gaaggtgaga a                    21

<210> SEQ ID NO 64
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
gacaaccctg actaccagca gga                    23

<210> SEQ ID NO 65
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
caaccctgac taccagcagg act                    23

<210> SEQ ID NO 66
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
ccctgactac cagcaggact tct                    23

<210> SEQ ID NO 67
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67 caggggatg aaagaatgca ttt                    23

<210> SEQ ID NO 68
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
ggatgaaaga atgcatttgc caa                    23

<210> SEQ ID NO 69
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
gaattctcca aaatggcccg aga                    23

```
<210> SEQ ID NO 70
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
cgatgtctac atgatcatgg tca                                            23

<210> SEQ ID NO 71
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
ctacatgatc atggtcaagt gct                                            23

<210> SEQ ID NO 72
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
ggcaaagtgc ctatcaagtg gat                                            23

<210> SEQ ID NO 73
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
ctctggatcc cagaaggtga gaa                                            23

<210> SEQ ID NO 74
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
gacaaccctg actaccagca ggact                                          25

<210> SEQ ID NO 75
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
ggggatgaaa gaatgcattt gccaa                                          25

<210> SEQ ID NO 76
```

```
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
ccatcgatgt ctacatgatc atggt                                         25

<210> SEQ ID NO 77
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
gatgtctaca tgatcatggt caagt                                         25

<210> SEQ ID NO 78
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
gtctacatga tcatggtcaa gtgct                                         25

<210> SEQ ID NO 79
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
gatcatggtc aagtgctgga tgata                                         25

<210> SEQ ID NO 80
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
gatcacagat tttgggctgg ccaaa                                         25

<210> SEQ ID NO 81
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
cagattttgg gctggccaaa ctgct                                         25

<210> SEQ ID NO 82
<211> LENGTH: 25
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 82
cacagatttt gggctggcca aactg                                          25

<210> SEQ ID NO 83
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
ctctggatcc cagaaggtga gaaag                                          25

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
caccagacag gtgttatgga a                                              21

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
cagacaggtg ttatggaagc t                                              21

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
ggtgttatgg aagctgctga a                                              21

<210> SEQ ID NO 87
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
ggaagctgct gaaggttgtg a                                              21

<210> SEQ ID NO 88
<211> LENGTH: 21
<212> TYPE: DNA
<213> ORGANISM: Artificial Sequence
<220> FEATURE:
```

-continued

<223> OTHER INFORMATION: Description of Artificial Sequence: Synthetic
     oligonucleotide

<400> SEQUENCE: 88
gctgctgaag gttgtgaaat t                                              21

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 89
gaaggttgtg aaattcggag a                                              21

<210> SEQ ID NO 90
<211> LENGTH: 21
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 90
cagcaattag cagccctggc a                                              21

<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 91
cagccctggc aggcaacccc a                                              21

<210> SEQ ID NO 92
<211> LENGTH: 21
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 92
gccctggcag gcaaccccaa a                                              21

<210> SEQ ID NO 93
<211> LENGTH: 22
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 93
ccagacaggt gttatggaag ct                                             22

<210> SEQ ID NO 94
<211> LENGTH: 22
<212> TYPE: DNA
<213> ORGANISM: Artificial Sequence
<220> FEATURE:
<223> OTHER INFORMATION: Description of Artificial Sequence: Synthetic
     oligonucleotide

```
<400> SEQUENCE: 94
gacaggtgtt atggaagctg ct                                              22

<210> SEQ ID NO 95
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
caggtgttat ggaagctgct ga                                              22

<210> SEQ ID NO 96
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
gttatggaag ctgctgaagg tt                                              22

<210> SEQ ID NO 97
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
ggaagctgct gaaggttgtg aa                                              22

<210> SEQ ID NO 98
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
gctgaaggtt gtgaaattcg ga                                              22

<210> SEQ ID NO 99
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
gaaggttgtg aaattcggag aa                                              22

<210> SEQ ID NO 100
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
```

```
cttaccagca attagcagcc ct                                          22

<210> SEQ ID NO 101
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
ccagcaatta gcagccctgg ca                                          22

<210> SEQ ID NO 102
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
gcagccctgg caggcaaccc ca                                          22

<210> SEQ ID NO 103
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 103
ccagacaggu guuauggaag cugcu                                       25

<210> SEQ ID NO 104
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104
gacagguguu auggaagcug cugaa                                       25

<210> SEQ ID NO 105
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 105
gguguuaugg aagcugcuga agguu                                       25

<210> SEQ ID NO 106
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 106
ggaagcugcu gaagguugug aaauu                                       25
```

<210> SEQ ID NO 107
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 107
cagcaauuag cagcccuggc aggca                                          25

<210> SEQ ID NO 108
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108
cuuaccagca auuagcagcc cuggc                                          25

<210> SEQ ID NO 109
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109
ccagcaauua gcagcccugg caggc                                          25

<210> SEQ ID NO 110
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110
gcaauuagca gcccuggcag gcaac                                          25

<210> SEQ ID NO 111
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
cccttgtttc cgctgcatcc a                                              21

<210> SEQ ID NO 112
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
catcatcaag ttccccggcg a                                              21

```
<210> SEQ ID NO 113
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
gacaaagagt tggcagtgca a                                              21

<210> SEQ ID NO 114
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
gcaacccaga tgtggccaac t                                              21

<210> SEQ ID NO 115
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
caagcccaag tgggacaaga a                                              21

<210> SEQ ID NO 116
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
gcccaagtgg gacaagaacc a                                              21

<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
caactttgag aaggatggca a                                              21

<210> SEQ ID NO 118
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
gatggcatcg ctcagatccg t                                              21

<210> SEQ ID NO 119
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
cctggatgcc gtcgtggacc t                                              21

<210> SEQ ID NO 120
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
gccagggatc tcttcaatgc t                                              21

<210> SEQ ID NO 121
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
cccttgtttc cgctgcatcc aga                                            23

<210> SEQ ID NO 122
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
ccatcatcaa gttccccggc gat                                            23

<210> SEQ ID NO 123
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
gacaaagagt tggcagtgca ata                                            23

<210> SEQ ID NO 124
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
ggcaacccag atgtggccaa cta                                            23

<210> SEQ ID NO 125
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 125
cgcaagccca agtgggacaa gaa                                             23

<210> SEQ ID NO 126
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
gcccaagtgg gacaagaacc aga                                             23

<210> SEQ ID NO 127
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
ggacaagaac cagatcacat aca                                             23

<210> SEQ ID NO 128
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
caactttgag aaggatggca agt                                             23

<210> SEQ ID NO 129
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
ggcatcgctc agatccgtgg tga                                             23

<210> SEQ ID NO 130
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
ctggatgccg tcgtggacct gca                                             23

<210> SEQ ID NO 131
<211> LENGTH: 25
<212> TYPE: DNA
<213> ORGANISM: Artificial Sequence
<220> FEATURE:
<223> OTHER INFORMATION: Description of Artificial Sequence: Synthetic
```

```
oligonucleotide

<400> SEQUENCE: 131
cccttgtttc cgctgcatcc agact                                               25

<210> SEQ ID NO 132
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
ccatcatcaa gttccccggc gatgt                                               25

<210> SEQ ID NO 133
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
gagttggcag tgcaatacct gaaca                                               25

<210> SEQ ID NO 134
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
gcaacccaga tgtggccaac tacaa                                               25

<210> SEQ ID NO 135
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
gcaagcccaa gtgggacaag aacca                                               25

<210> SEQ ID NO 136
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
cccaagtggg acaagaacca gatca                                               25

<210> SEQ ID NO 137
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 137
gacaagaacc agatcacata cagga                                              25

<210> SEQ ID NO 138
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
ggcatcgctc agatccgtgg tgaga                                              25

<210> SEQ ID NO 139
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
gagcgtgaag tttggaagca tcaaa                                              25

<210> SEQ ID NO 140
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
gagatcttct tcttcaagga ccggt                                              25

<210> SEQ ID NO 141
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
catccagttt ggtgtcgcgg a                                                  21

<210> SEQ ID NO 142
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
ccagtttggt gtcgcggagc a                                                  21

<210> SEQ ID NO 143
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
```
gcggagcacg gagacgggta t                                              21

<210> SEQ ID NO 144
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
cggagacggg tatcccttcg a                                              21

<210> SEQ ID NO 145
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
gagctgtgcg tcttcccctt c                                              21

<210> SEQ ID NO 146
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
gtcatccagt ttggtgtcgc gga                                            23

<210> SEQ ID NO 147
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
gcgcggagca cggagacggg tat                                            23

<210> SEQ ID NO 148
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
ggagcacgga gacgggtatc cct                                            23

<210> SEQ ID NO 149
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
ccagtttggt gtcgcggagc acgga                                          25

-continued

```
<210> SEQ ID NO 150
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
cgcgcgcgga gcacggagac gggta                                               25

<210> SEQ ID NO 151
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
cggagcacgg agacgggtat ccctt                                               25

<210> SEQ ID NO 152
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 152
ccaccacaac aucaccuaut t                                                   21

<210> SEQ ID NO 153
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 153
auaggugaug uugugguggt t                                                   21

<210> SEQ ID NO 154
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 154
gccaguuucc auucaucuut t                                                   21

<210> SEQ ID NO 155
<211> LENGTH: 21
<212> TYPE: DNA
<213> ORGANISM: Artificial Sequence
<220> FEATURE:
```

```
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 155
aagaugaaug gaaacuggct t                                              21

<210> SEQ ID NO 156
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 156
gcgcugggcu uagaucauut t                                              21

<210> SEQ ID NO 157
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 157
aaugaucuaa gcccagcgct t                                              21

<210> SEQ ID NO 158
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 158
gcauaaggac gacgugaaut t                                              21

<210> SEQ ID NO 159
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 159
auucacgucg uccuuaugct t                                              21

<210> SEQ ID NO 160
<211> LENGTH: 21
<212> TYPE: DNA
<213> ORGANISM: Artificial Sequence
<220> FEATURE:
```

<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 160
ccugcaacgu gaacaucuut t                                              21

<210> SEQ ID NO 161
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 161
aagauguuca cguugcaggt t                                              21

<210> SEQ ID NO 162
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 162
ggaaccagcu guauuuguut t                                              21

<210> SEQ ID NO 163
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 163
aacaaauaca gcugguucct t                                              21

<210> SEQ ID NO 164
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 164
gccaguuugc cggauacaat t                                              21

<210> SEQ ID NO 165
<211> LENGTH: 21
<212> TYPE: DNA
<213> ORGANISM: Artificial Sequence
<220> FEATURE:

```
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 165
uuguauccgg caaacuggct t                                              21

<210> SEQ ID NO 166
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 166
ccaguuugcc ggauacaaat t                                              21

<210> SEQ ID NO 167
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 167
uuuguauccg gcaaacuggt t                                              21

<210> SEQ ID NO 168
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 168
gccggauaca aacugguaut t                                              21

<210> SEQ ID NO 169
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 169
auaccaguuu guauccggct t                                              21

<210> SEQ ID NO 170
<211> LENGTH: 21
<212> TYPE: DNA
<213> ORGANISM: Artificial Sequence
<220> FEATURE:
```

```
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 170
ccggauacaa acugguauut t                                               21

<210> SEQ ID NO 171
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 171
aauaccaguu uguauccggt t                                               21

<210> SEQ ID NO 172
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 172
uggcaccacc acaacaucac cuauu                                           25

<210> SEQ ID NO 173
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 173
aauaggugau guuguggugg ugcca                                           25

<210> SEQ ID NO 174
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 174
cacaacauca ccuauuggau ccaaa                                           25

<210> SEQ ID NO 175
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 175
uuuggaucca auaggugaug uugug                                           25

<210> SEQ ID NO 176
```

```
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 176
gacgcagaca ucgucaucca guuug                                          25

<210> SEQ ID NO 177
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 177
caaacuggau gacgaugucu gcguc                                          25

<210> SEQ ID NO 178
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 178
ggaaacccug ccaguuucca uucau                                          25

<210> SEQ ID NO 179
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 179
augaauggaa acuggcaggg uuucc                                          25

<210> SEQ ID NO 180
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 180
cauucaucuu ccaaggccaa uccua                                          25

<210> SEQ ID NO 181
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 181
uaggauuggc cuuggaagau gaaug                                          25

<210> SEQ ID NO 182
<211> LENGTH: 25
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 182
acgaugccug caacgugaac aucuu                                          25

<210> SEQ ID NO 183
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 183
aagauguuca cguugcaggc aucgu                                          25

<210> SEQ ID NO 184
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 184
gcggagauug ggaaccagcu guauu                                          25

<210> SEQ ID NO 185
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 185
aauacagcug guucccaauc uccgc                                          25

<210> SEQ ID NO 186
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 186
cggagauugg gaaccagcug uauuu                                          25

<210> SEQ ID NO 187
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 187
aaauacagcu gguucccaau cuccg                                          25

<210> SEQ ID NO 188
<211> LENGTH: 25
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 188
caguaccgag agaaagccua uuucu                                              25

<210> SEQ ID NO 189
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 189
agaaauaggc uuucucucgg uacug                                              25

<210> SEQ ID NO 190
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 190
aagccuauuu cugccaggac cgcuu                                              25

<210> SEQ ID NO 191
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 191
aagcgguccu ggcagaaaua ggcuu                                              25

<210> SEQ ID NO 192
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
caccctcctc cgggccgcgc t                                                  21

<210> SEQ ID NO 193
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
ctcctccggg ccgcgctccc t                                                  21

<210> SEQ ID NO 194
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

-continued

<210> SEQ ID NO 195
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
ctgaatttcg ccgccacagg a                                              21

<210> SEQ ID NO 196
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
ggagcgcccg ccccgcggcc t                                              21

<210> SEQ ID NO 197
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
ctgctgctcc tcggctgcgg a                                              21

<210> SEQ ID NO 198
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
gctgctcctc ggctgcggat a                                              21

<210> SEQ ID NO 199
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
gatccacagc atccgggacc t                                              21

<210> SEQ ID NO 200
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200

```
ccacagcatc cgggacctcc a                                              21
```

<210> SEQ ID NO 201
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201

```
catccgggac ctccagcgac t                                              21
```

<210> SEQ ID NO 202
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202

```
gccaccctcc tccgggccgc gct                                            23
```

<210> SEQ ID NO 203
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203

```
ccctcctccg ggccgcgctc cct                                            23
```

<210> SEQ ID NO 204
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204

```
gatggtactg aatttcgccg cca                                            23
```

<210> SEQ ID NO 205
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205

```
ctggagcgcc cgccccgcgg cct                                            23
```

<210> SEQ ID NO 206
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206

```
gcgcccgccc cgcggcctcg cct                                            23
```

<210> SEQ ID NO 207
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
gcctcgggac gcgatgagga cct                                              23

<210> SEQ ID NO 208
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
ggcttgcctg ctgctcctcg gct                                              23

<210> SEQ ID NO 209
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
gcctgctgct cctcggctgc gga                                              23

<210> SEQ ID NO 210
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
cagatccaca gcatccggga cct                                              23

<210> SEQ ID NO 211
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
gaccaggacg gtcatttacg aga                                              23

<210> SEQ ID NO 212
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
gcgccaccct cctccgggcc gcgct                                            25

```
<210> SEQ ID NO 213
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
caccctcctc cgggccgcgc tccct                                              25

<210> SEQ ID NO 214
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
gggatggtac tgaatttcgc cgcca                                              25

<210> SEQ ID NO 215
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
gatggtactg aatttcgccg ccaca                                              25

<210> SEQ ID NO 216
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216
ggtactgaat tcgccgcca cagga                                               25

<210> SEQ ID NO 217
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
ggctggagcg cccgccccgc ggcct                                              25

<210> SEQ ID NO 218
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
gagcgcccgc ccgcggcct cgcct                                               25

<210> SEQ ID NO 219
<211> LENGTH: 25
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
ccagcgcctc gggacgcgat gagga                                            25

<210> SEQ ID NO 220
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
gcgcctcggg acgcgatgag gacct                                            25

<210> SEQ ID NO 221
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
gcctgctgct cctcggctgc ggata                                            25

<210> SEQ ID NO 222
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 222
gaugucuaca ugaucauggu caagu                                            25

<210> SEQ ID NO 223
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 223
acuugaccau gaucauguag acauc                                            25

<210> SEQ ID NO 224
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 224
gucuacauga ucauggucaa gugcu                                            25

<210> SEQ ID NO 225
<211> LENGTH: 25
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 225
agcacuugac caugaucaug uagac                                          25

<210> SEQ ID NO 226
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 226
gaucacagau uuugggcugg ccaaa                                          25

<210> SEQ ID NO 227
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 227
uuuggccagc ccaaaaucug ugauc                                          25

<210> SEQ ID NO 228
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 228
cagauuuugg gcuggccaaa cugcu                                          25

<210> SEQ ID NO 229
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 229
agcaguuugg ccagcccaaa aucug                                          25

<210> SEQ ID NO 230
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 230
cacagauuuu gggcuggcca aacug                                          25

<210> SEQ ID NO 231
<211> LENGTH: 25
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 231
caguuuggcc agcccaaaau cugug                                   25

<210> SEQ ID NO 232
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 232
cucuggaucc cagaagguga gaaag                                   25

<210> SEQ ID NO 233
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 233
cuuucucacc uucugggauc cagag                                   25

<210> SEQ ID NO 234
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 234
ccaugccaag uggucccagg cugca                                   25

<210> SEQ ID NO 235
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 235
ugcagccugg gaccacuugg caugg                                   25

<210> SEQ ID NO 236
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 236
ccaacaucac caugcagauu augcg                                   25

<210> SEQ ID NO 237
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 237
cgcauaaucu gcauggugau guugg                                         25

<210> SEQ ID NO 238
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 238
cacuuugggu ccggagggcg agacu                                         25

<210> SEQ ID NO 239
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 239
agucucgccc uccggaccca aagug                                         25

<210> SEQ ID NO 240
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 240
cgcagacgug uaaauguucc ugcaa                                         25

<210> SEQ ID NO 241
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 241
uugcaggaac auuuacacgu cugcg                                         25

<210> SEQ ID NO 242
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 242
aaccuucagc agcuuccaua acacc                                         25

<210> SEQ ID NO 243
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 243
aauuucacaa ccuucagcag cuucc                                              25

<210> SEQ ID NO 244
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 244
ugccugccag ggcugcuaau ugcug                                              25

<210> SEQ ID NO 245
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 245
gccagggcug cuaauugcug guaag                                              25

<210> SEQ ID NO 246
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 246
gccugccagg gcugcuaauu gcugg                                              25

<210> SEQ ID NO 247
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 247
guugccugcc agggcugcua auugc                                              25

<210> SEQ ID NO 248
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 248
uauccgcagc cgaggagcag caggc                                              25

<210> SEQ ID NO 249
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 249
cccaaguggg acaagaacca gauca                                          25

<210> SEQ ID NO 250
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 250
ugaucugguu cuugucccac uuggg                                          25

<210> SEQ ID NO 251
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 251
ccaguuuggu gucgcggagc acgga                                          25

<210> SEQ ID NO 252
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 252
uccgugcucc gcgacaccaa acugg                                          25

<210> SEQ ID NO 253
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Asp Cys Arg Asp Trp Lys Thr Cys Thr
1               5

<210> SEQ ID NO 254
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 254

Tyr Thr Ile Trp Met Pro Glu Asn Pro Arg Pro Gly Thr Pro Cys Asp
1               5                   10                  15

Ile Phe Thr Asn Ser Arg Gly Lys Arg Ala Ser Asn Gly Gly Gly Gly
            20                  25                  30

Arg Arg Arg Arg Arg Arg Arg Arg Arg
        35                  40

```
<210> SEQ ID NO 255
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Lys His His His Lys His His His Lys His His His Lys His His His
1               5                   10                  15

Lys

<210> SEQ ID NO 256
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Lys His His His Lys His His His Asn His His His Asn His His His
1               5                   10                  15

Asn
```

US 8,541,568 B2

COMPOSITIONS AND METHODS USING SIRNA MOLECULES FOR TREATMENT OF GLIOMAS

This application claims priority to U.S. Provisional Patent Application No. 61/055,966, filed May 24, 2008, which is incorporated herein by reference in its entirety.

FIELD OF THE INVENTION

This application is a U.S. national phase application of, and claims priority to and the benefit of, International Patent Application No. PCT/US2009/003196, filed May 26, 2009, which claims priority to, and the benefit of, U.S. Provisional Patent Application No. 61/055,966, filed May 24, 2008. The disclosures of these applications are expressly incorporated herein by reference in their entireties.

BACKGROUND

Major advances in molecular biology, cellular biology, and genomics have substantially improved our understanding of cancer. Now, these advances are being translated into therapy. Targeted therapy directed at specific molecular alterations is already creating a shift in the treatment of cancer patients. Glioblastoma multiforme (GBM), the most common brain cancer of adults, is highly suited for this new approach. GBM is among the most aggressive and deadly of neoplasms. Despite decades of aggressive surgical treatment, chemotherapy, radiotherapy, and extensive basic science and clinical research focused on combating this disease, the prognosis remains virtually unchanged, with survival rates still measured in months. The current genetic understanding of GBM has led to the identification of crucial intracellular molecules and their associated signaling pathways as potential therapeutic targets. Multiple genes are being identified as critical to the development of GBM and other similar tumors, such as gliomas and other astrocytomas.

Targets Involved in GBM

GBM, like most malignant tumors, exhibits multiple genetic abnormalities, including aberrant activation of intracellular signal-transduction pathways that regulate processes such as proliferation, angiogenesis, and apoptosis. For example, vascular endothelial growth factor (VEGF) is needed to promote tumorigenesis and angiogenesis in GBM (7). In addition, over 40% of all GBMs exhibit amplification, mutation, or rearrangement of the epidermal growth factor receptor (EGFR) (2). As is common in malignant neoplasms, EGFR overexpression leads to aberrant activation of crucial downstream targets, including the PI3K/AKT signaling pathway, which mediates cell survival, and the mitogenic RAS/MAPK cascade. Recent studies implicate a mutant variant of EGFR, EGFRvIII, in the activation of other receptor tyrosine kinases (RTKs), such as MET, thereby providing multiple inputs to these downstream signaling pathways for cellular proliferation and evasion of apoptosis. This redundant signaling could partially account for the modest response of GBMs to RTK inhibitors, such as erlotinib and gefitinib. In addition, GBM is frequently associated with elevated levels of $O^6$-methylguanine-DNA-methyltransferase (AGT), a DNA repair enzyme that enhances neoplastic resistance to chemotherapeutics such as Temozolomide (TMZ).

Matrix metalloproteinases (MMPs) enhance tumor cell invasion by degrading extracellular matrix proteins, by activating signal transduction cascades that promote motility, and by solubilizing extracellular matrix-bound growth factors. MMP-9 and MMP-2 promote GBM invasion in vitro and in xenograft models, and their inhibition dramatically reduces the invasive phenotype (1). The serine/threonine kinase Raf-1 is involved in the regulation of tumor cell survival, proliferation and metastasis formation, and has therefore emerged as a promising target for cancer therapy. Raf-1 silencing appears as a potential therapeutic strategy to inhibit brain tumor angiogenesis and thereby outgrowth of highly vascularized glioblastoma multiforme (28). RNA interference targeting TGF-beta 1, 2 results in a glioma cell phenotype that is more sensitive to immune cell lysis and less motile in vitro and nontumorigenic in nude mice (29). The mammalian target of rapamycin (mTOR) activity is required for the survival of some cells within these GBMs, and mTOR appears required for the maintenance of astrocytic character in the surviving cells (30). A small molecule inhibitor of Cox-2 enhanced glioblastoma radiosensitivity, reduced tumor cell viability and prolonged survival of implanted glioblastoma mice by inhibition of tumor angiogenesis and causing extensive tumor necrosis (31).

RNA Interference (RNAi) and Small Interfering RNA (siRNA)

RNA interference (RNAi) is a sequence-specific RNA degradation process that provides a relatively easy and direct way to knock down, or silence, theoretically any gene. In naturally occurring RNAi, a double-stranded RNA (dsRNA) is cleaved by an RNase III/helicase protein, Dicer, into small interfering RNA (siRNA) molecules, a dsRNA of 19-27 nucleotides (nt) with 2-nt overhangs at the 3' ends. These siRNAs are incorporated into a multicomponent-ribonuclease called RNA-induced silencing complex (RISC). One strand of siRNA remains associated with RISC and guides the complex toward a cognate RNA that has sequence complementary to the guider ss-siRNA in RISC. This siRNA-directed endonuclease digests the RNA, thereby inactivating it. Recent studies have revealed that chemically synthesized 21-27-nt siRNAs exhibit RNAi effects in mammalian cells, and the thermodynamic stability of siRNA hybridization (at terminals or in the middle) plays a central role in determining the molecule's function. These and other characteristics of RISC, siRNA molecules, and RNAi have been described.

Applications of RNAi in mammalian cells in the laboratory or, potentially, in therapeutic settings, use either chemically synthesized siRNAs or endogenously expressed molecules. The endogenous siRNA is first expressed as small hairpin RNAs (shRNAs) by an expression vector (plasmid or virus vector) and is then processed by Dicer into siRNAs. It is thought that siRNAs hold great promise to be therapeutics for human diseases, especially those caused by viral infections. Certain siRNA therapeutics are described in PCT application PCT/US2005/003858 for "Compositions and Methods for Combination RNAi Therapeutics", which is incorporated herein by reference in its entirety.

Importantly, it is presently not possible to predict with any degree of confidence which of many possible candidate siRNA sequences potentially targeting a genomic sequence (e.g., oligonucleotides of about 16-30 base pairs) will in fact exhibit effective siRNA activity. Instead, individual, specific candidate siRNA polynucleotide or oligonucleotide sequences must be generated and tested to determine whether the intended interference with expression of a targeted gene has occurred. Accordingly, no routine method exists for designing an siRNA polynucleotide that is, with certainty, capable of specifically altering the expression of a given mRNA.

SUMMARY OF THE INVENTION

The present invention provides an isolated small interfering RNA (siRNA) molecule that binds to a single-stranded RNA molecule, wherein the single-stranded RNA molecule comprises an mRNA that encodes at least part of a peptide or protein whose activity promotes tumorigenesis, angiogenesis, or cell proliferation in the brain or spinal cord of a mammal, or wherein the single stranded RNA molecule comprises an miRNA whose activity promotes tumorigenesis, angiogenesis, or cell proliferation in the brain or spinal cord of a mammal.

The invention also provides a composition comprising at least three of the siRNA molecules. In one embodiment, the molecules bind to multiple, different target sequences in the single-stranded RNA molecule or in different single stranded RNA molecules.

The invention further provides compositions comprising one or more of the siRNA molecules in a pharmaceutically acceptable carrier. These compositions may include, or be used with, a therapeutic agent that prevents or hinders tumorigenesis, angiogenesis, or cell proliferation in the brain or spinal cord of a mammal.

The invention also provides a method for treating a glioma in a subject comprising administering to the subject an effective amount of a composition of the invention. In one embodiment, the subject is a human. In another embodiment, the glioma is a glioblastoma multiforme (GBM).

250 µl of Optimem I Reduced Serum Medium+1.4 µl siRNA (0.5 µg) (28 pmole/well)

250 µl of Optimem I Reduced Serum Medium+2.8 µl siRNA (1 µg) (56 pmole/well)

250 µl of Optimem I Reduced Serum Medium+5.6 µl (siRNA (2 µg) (112 pmole/well)

Small interfering ultimobranchial body cells were used for negative control (0.5 µg/well-28 pmole). After 6 hours, the medium was changed. mRNA was isolated by using an RNAqueous-4PCR kit.

Figure 1:
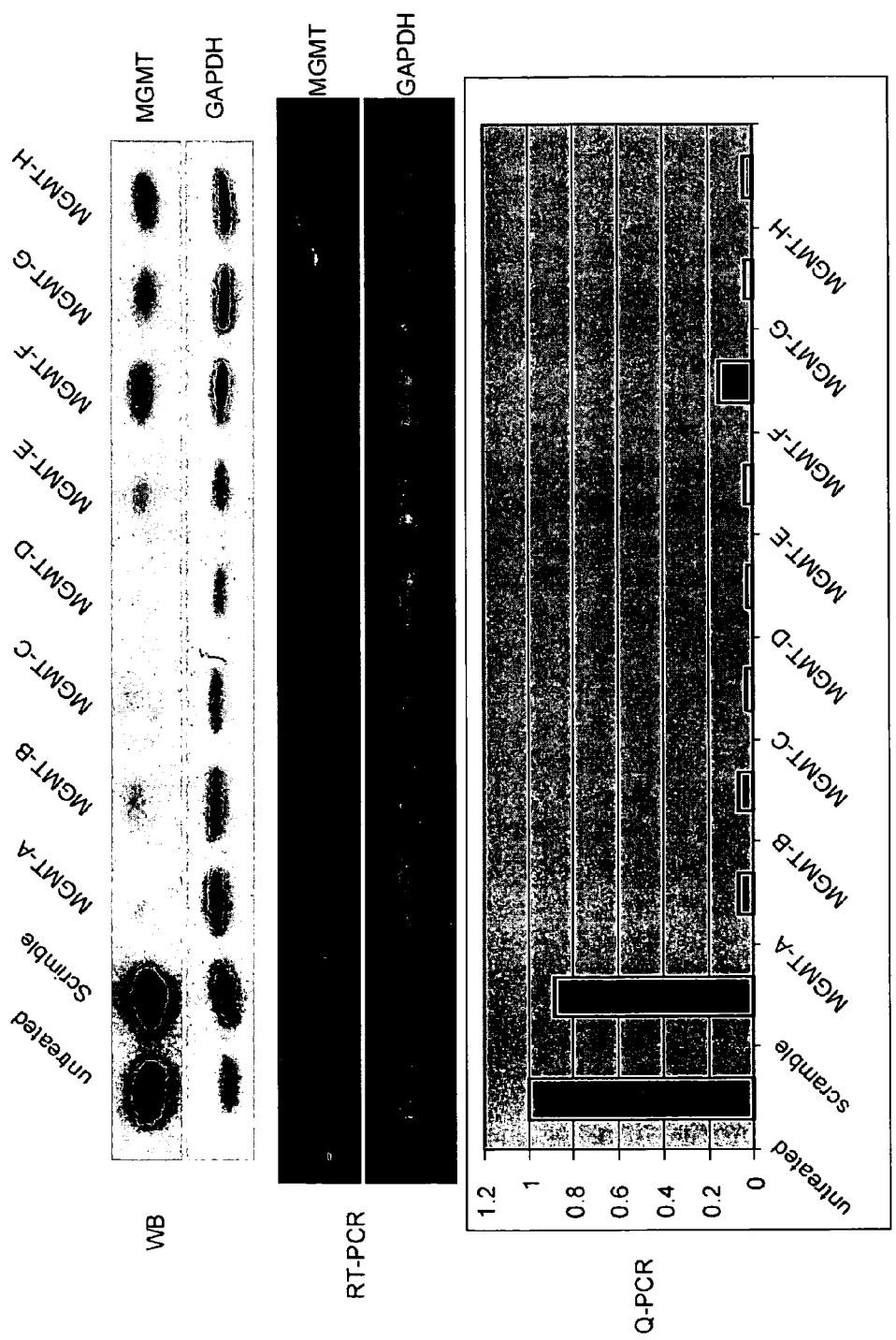
FIG. 1. Identification of siRNA duplexes silencing MGMT expression. The total RNA and protein samples were collected after H80TR cells were transfected with corresponding siRNA duplexes, followed by RT-PCR, quantitative PCR and Western blot analyses. Selection of potent siRNA duplexes targeting both human and mouse MGMT genes.
Figure 2:
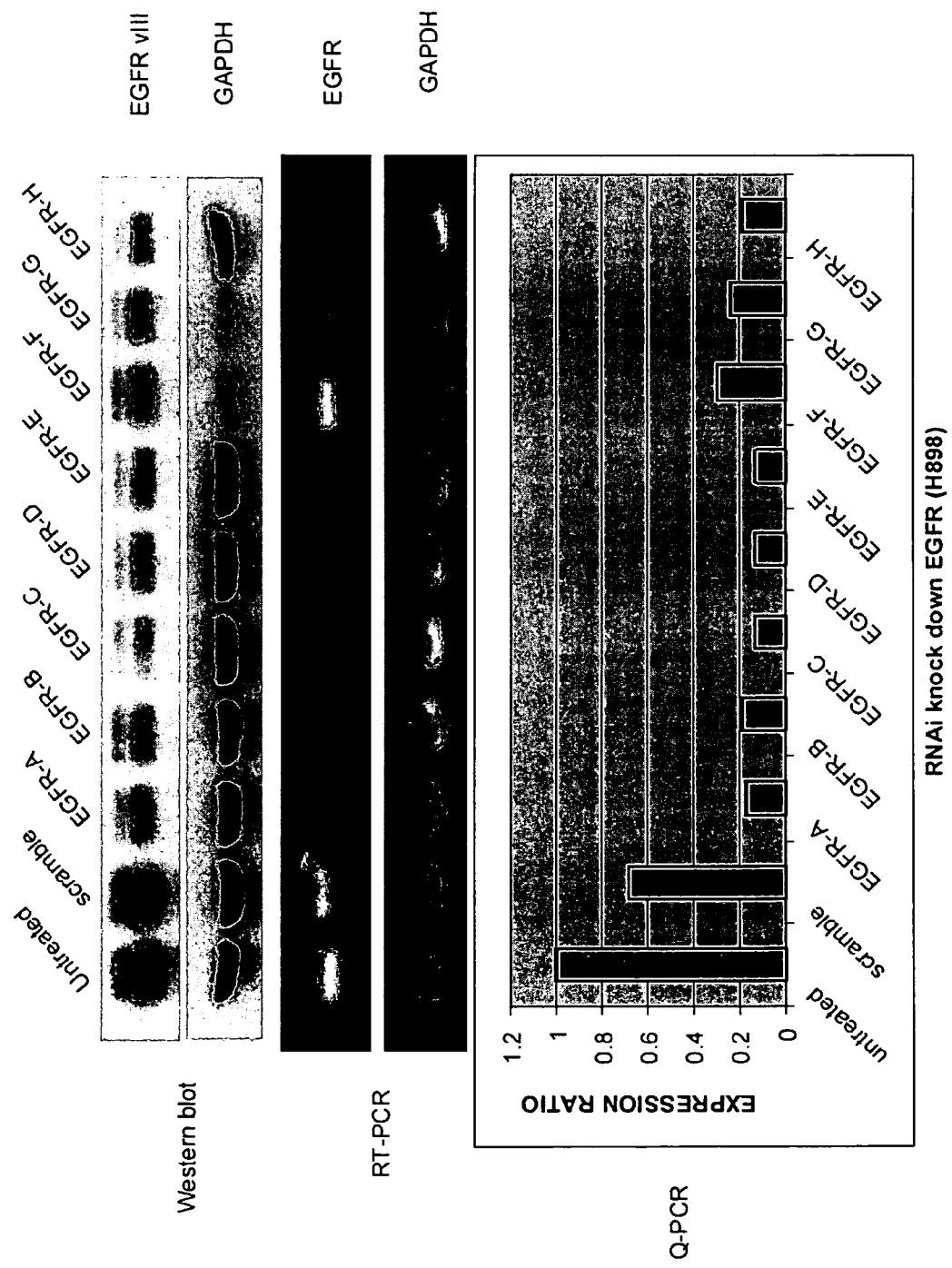
FIG. 2. Identification of siRNA duplexes silencing EGFR expression. The total RNA and protein samples were collected after H898 cells were transfected with corresponding siRNA duplexes, followed by RT-PCR, quantitative PCR and Western blot analyses. Selection of potent siRNA duplexes targeting both human and mouse EGFR.
Figure 3:
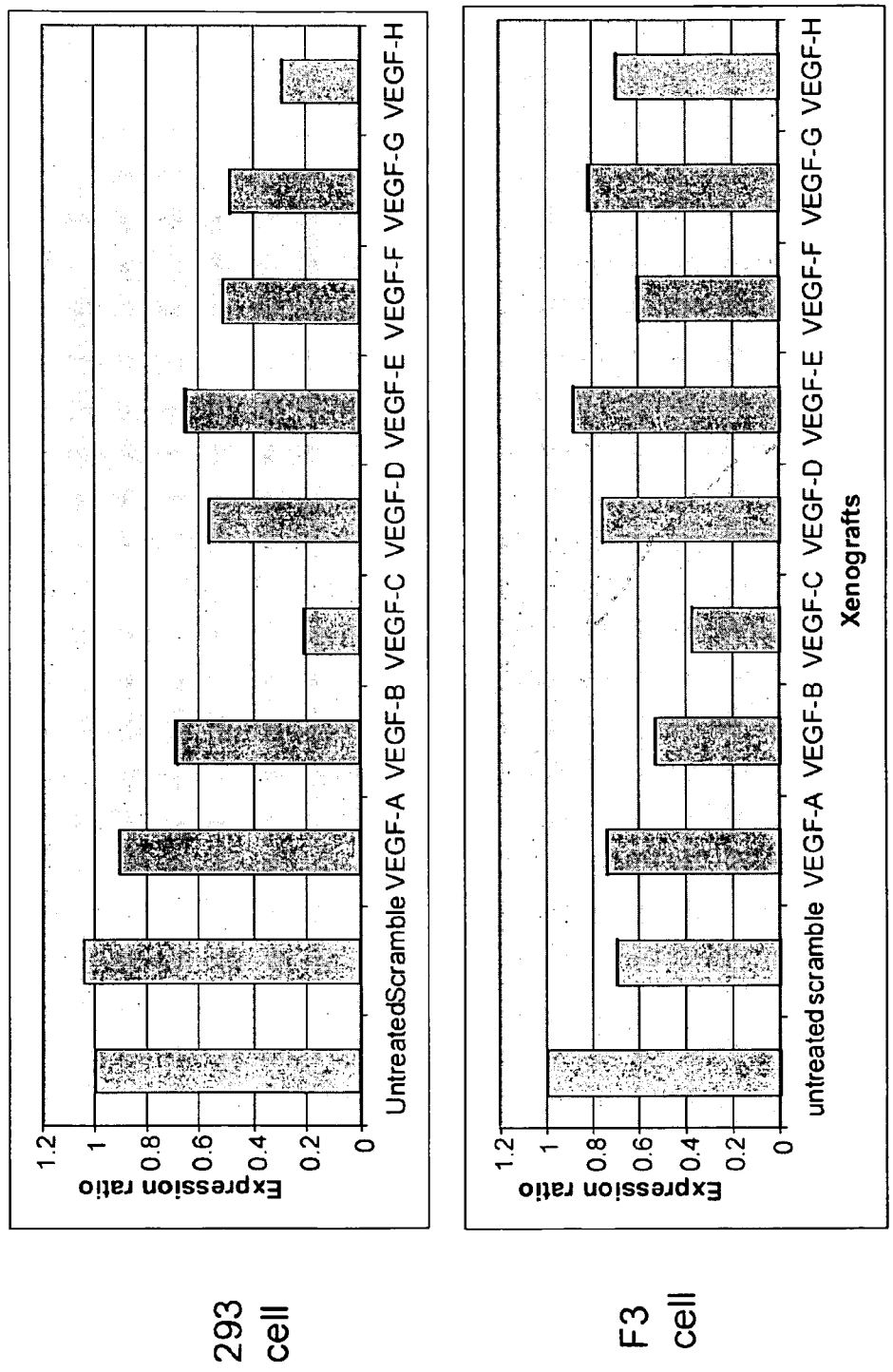
FIG. 3. Identification of potent siRNA duplexes silencing VEGF-A expression. The total RNA and protein samples were collected after 293 cells and F3 cells were transfected with corresponding siRNA duplexes, followed by quantitative PCR analyses. Selection of potent siRNA duplexes targeting both human and mouse VEGF.
Figure 4:
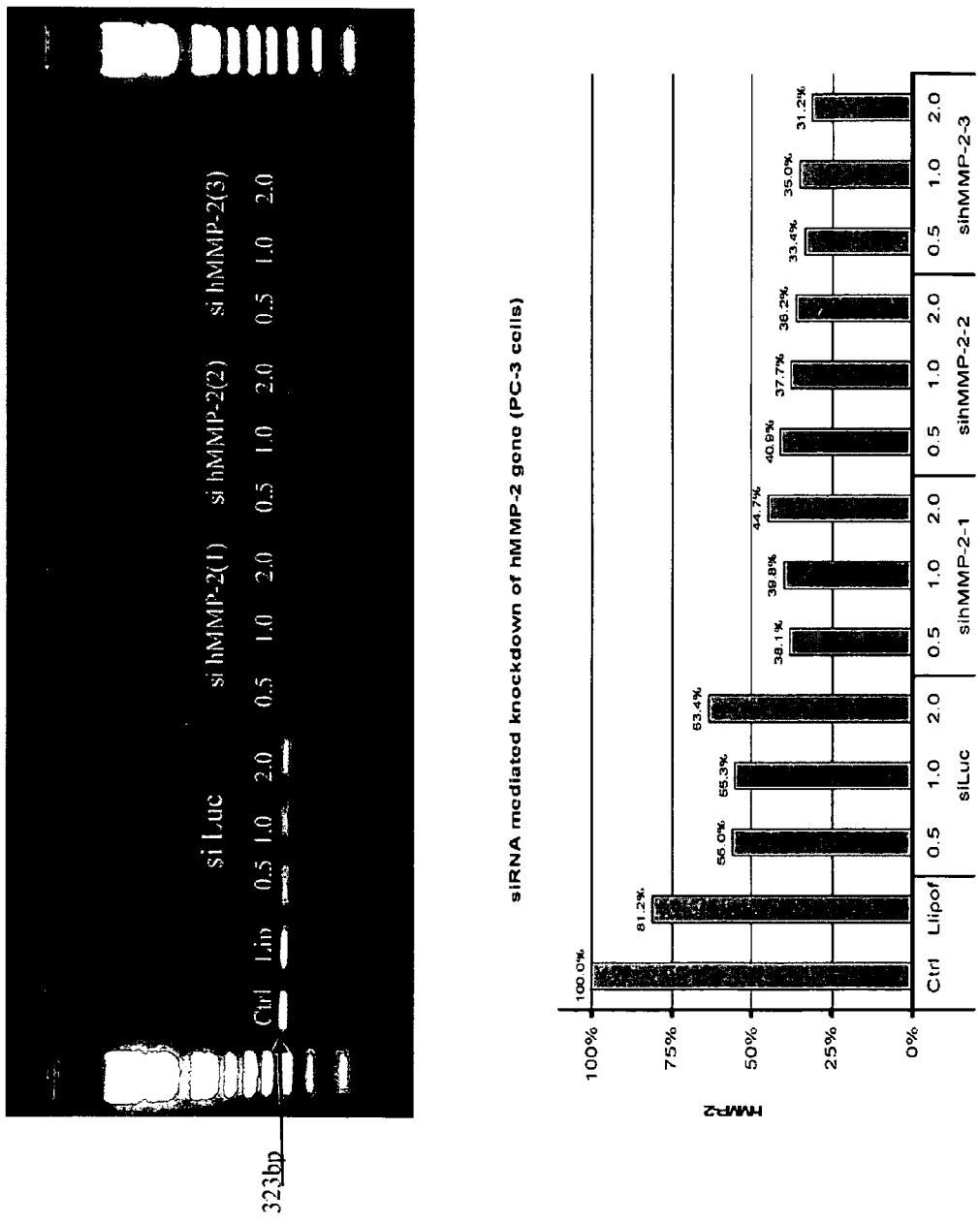
FIG. 4. Selection of potent siRNA for MMP-2 knockdown. On the day before transfection, $2.5 \times 10^5$ PC-3 cells were plated on the wells of 6-well plates in 2 ml of culture medium without antibiotics. On the next day, the cells were transfected with siRNA-hMMP-2 #1, #2, and #3 and Luc siRNA at different concentrations—0.5 µg/well, 1.0 µg/well, and 2.0 µg/well. For each transfection sample (in duplicate), oligomer-Lipofectamine 2000 complexes were prepared.
Figure 5:
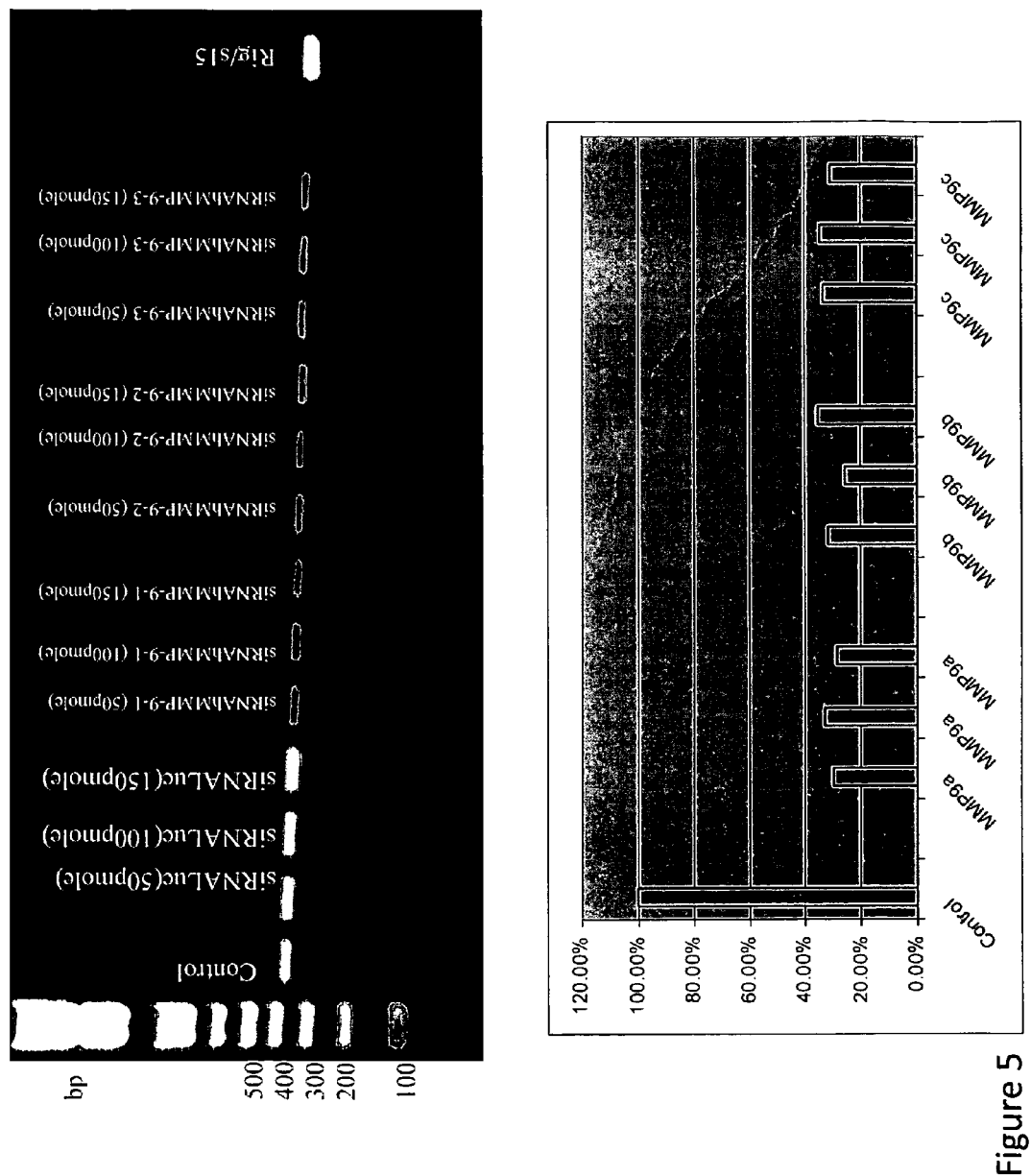

FIG. 5. Selection of potent MMP-9 siRNA. mRNA knockdown after transfection of the PC-3 cells with siRNA (hMMP-9). On the day before transfection, $2.5 \times 10^5$ PC-3 cells were plated on the wells of 6-well plates in 2 ml of culture medium without antibiotics. On the next day, cells were transfected with siRNA hMMP-9 #1, siRNA hMMP-9 #2, siRNA hMMP-9 #3, and siRNA Luc at different concentrations—0.9 µg/well (50 pmole), 1.8 µg/well (100 pmole), and 2.7 µg/well (150 pmole). After 6 hours, the medium was changed. Cells were incubated at 37° C. for 48 hours.

Figure 6:
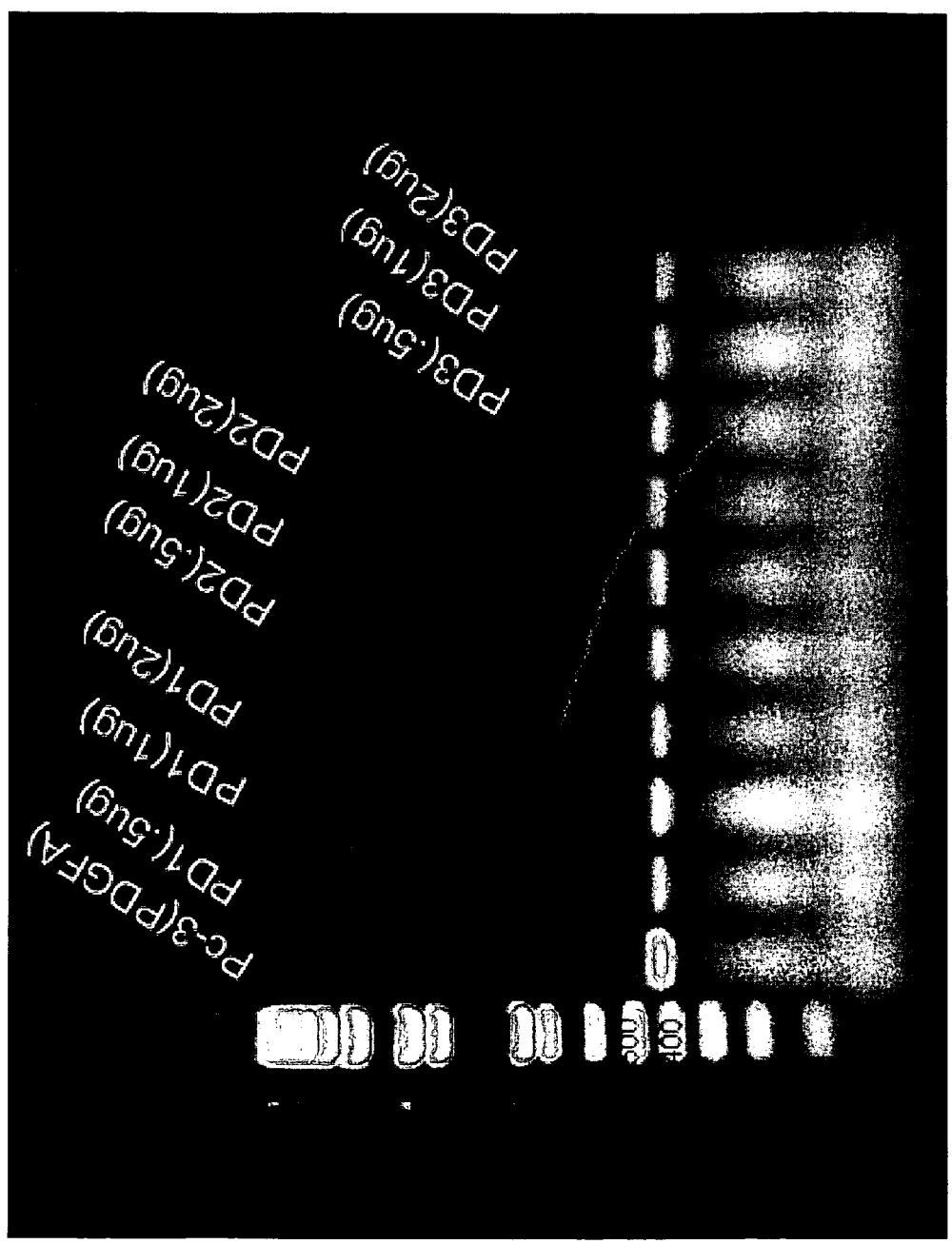

FIG. 6. Selection of potent PDGF siRNA using the same procedures as above.

Figure 7:
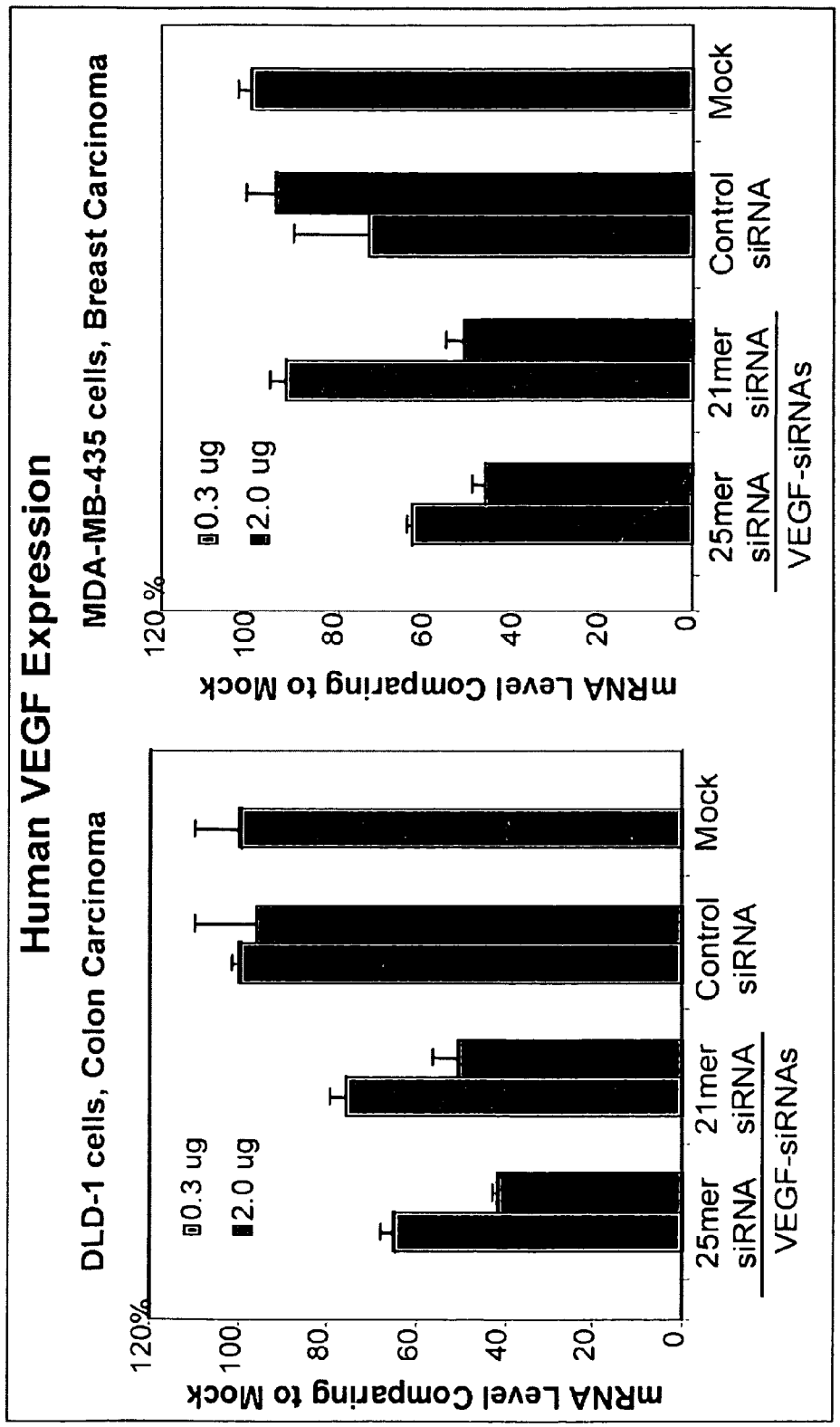

FIG. 7. Comparison of silencing potencies between 25mer and 21mer siRNA duplexes. The most potent 25 mer and 21mer siRNA were selected first from each set of 6 duplexes. Then comparison was carried out with two tumor cell lines expressing human VEGF protein (DLD-1, colon carcinoma and MBA-MD-435, breast carcinoma) using in vitro transfection with Lipo2000 (Invitrogen, CA) followed by RT-PCR analyses. At either 0.3 µg or 2.0 µg doses, 25mer siRNA demonstrated stronger inhibitory activity than 21mer siRNA, especially at 2.0 µg. We found that 25mer duplexes with blunt ends are the most potent inhibitors, up to 60% either MBA-MD-435 or DLD-1 cells and in tumor bearing in animals. We have tested a 25mer siRNA duplex targeting human VEGF gene, hVEGF-25c (sense: 5'-CACAACAAAUGUGAAUG-CAGACCAA-3' (SEQ ID NO: 1); Antisense: 5'-UUGGU-CUGCAUUCACAUUUGUUGUG-3' (SEQ ID NO: 2)), comparing to a 21mer siRNA duplex which has been tested many times as one of the most potent VEGF specific inhibitory duplexes, hVEGF-21a (sense: 5'-UCGAGACCCUG-GUGGACAUTT-3' (SEQ ID NO: 3); antisense: 5'-AUGUC-CACCAGGGUCUCGATT-3' (SEQ ID NO: 4)), in the cell culture followed with Q-RT-PCR analysis. FIG. 7 demonstrates that the 25 mer blunt end siRNA is more potent than the 21mer sticky end siRNA, which supports using 25mer siRNA duplexes in the proposed study of multi-targeted siRNA cocktail therapeutics for cancer treatment.

Figure 8:
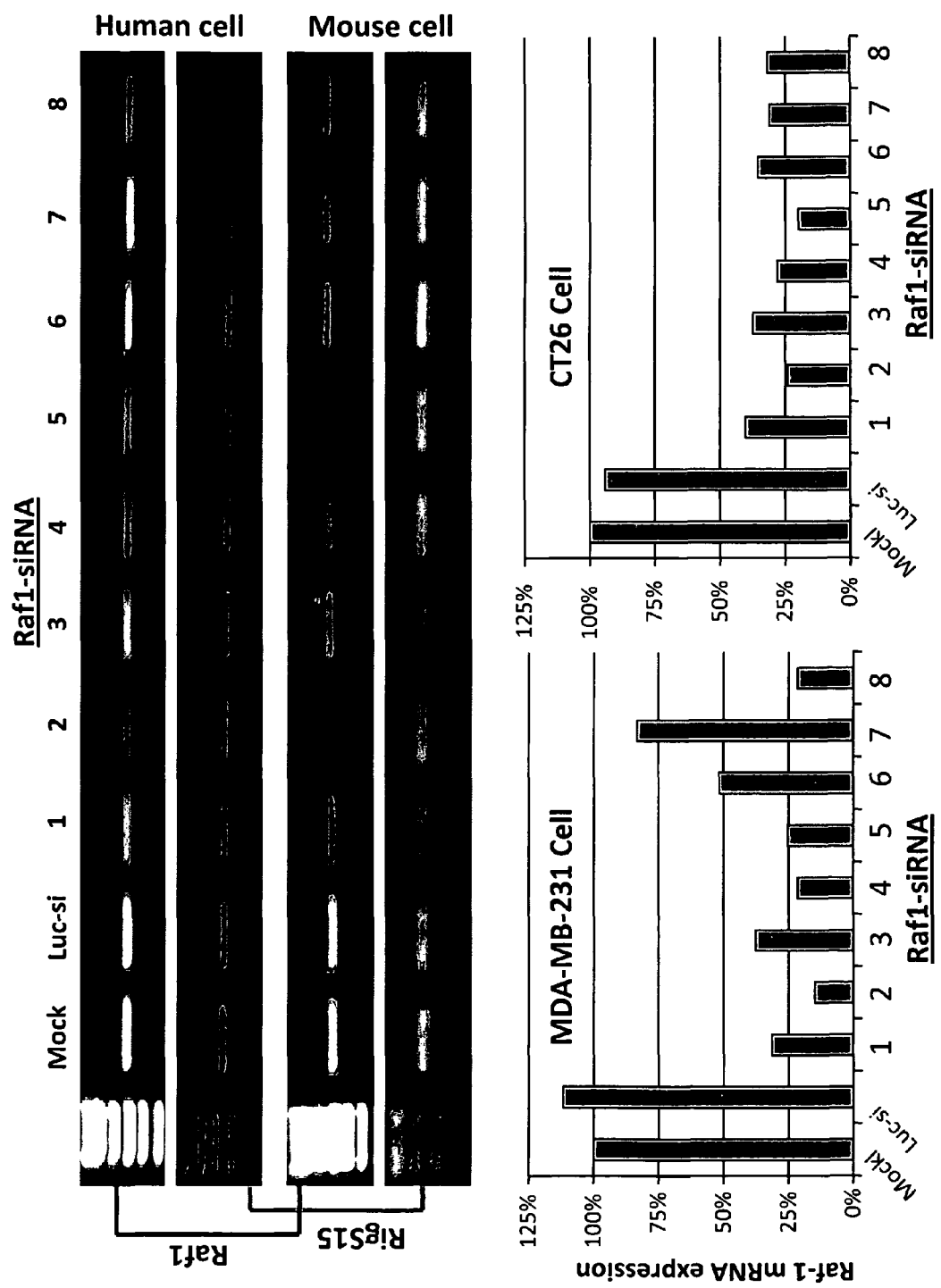

FIG. 8. Selection of potent siRNA targeting RAF-1. (A) The lower panel illustrates selection of eight 25 mer siRNA duplexes with control siRNA were transfected into human MDA-MB-231 cells and mouse CT26 cells. 24 hr later, mRNA were collected and subject to Q-RT-PCR with the standard control gene target Rigs15. Based on the gene silencing activity observed, the most potent Raf1-siRNA was selected as a component of a future siRNA cocktail for both in vitro and in vivo study. RAF-1-siRNA: 5'-GC-CUGCUGCUCCUCGGCUGCGGAUA-3' (SEQ ID NO: 5).

Figure 9:
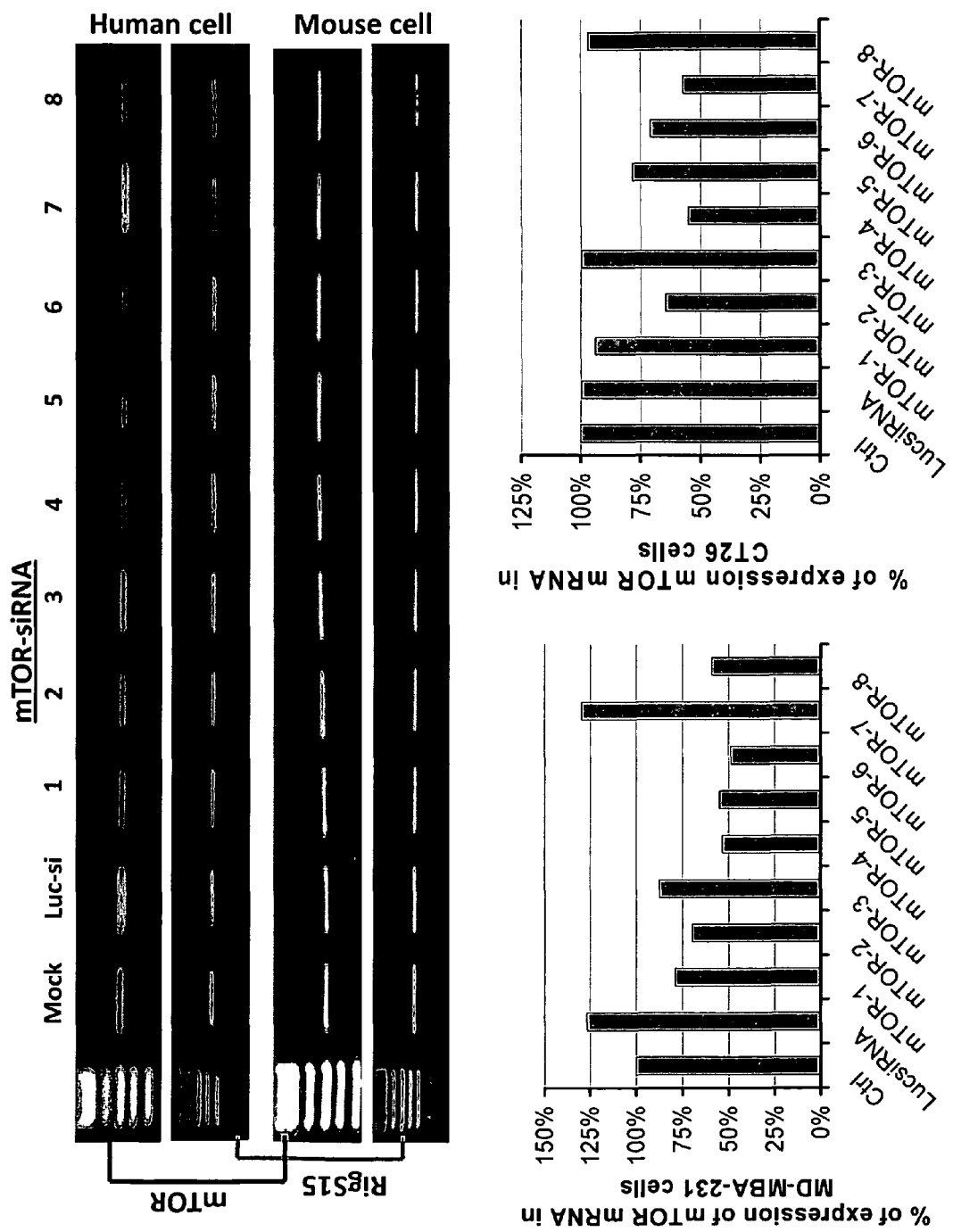

FIG. 9. Selection of potent siRNA targeting mTOR. (A) The lower panel illustrates selection of eight 25 mer siRNA duplexes with control siRNA were transfected into human MDA-MB-231 cells and mouse CT26 cells. 24 hr later, mRNA were collected and subject to Q-RT-PCR with the standard control gene target Rigs15. Based on the gene silencing activity observed, the most potent mTOR-siRNA was selected as a component of a future siRNA cocktail for both in vitro and in vivo study. mTOR-siRNA: 5'-GGUCUG-GUGCCUGGUCUGAUGAUGU-3' (SEQ ID NO: 6).

Figure 10:
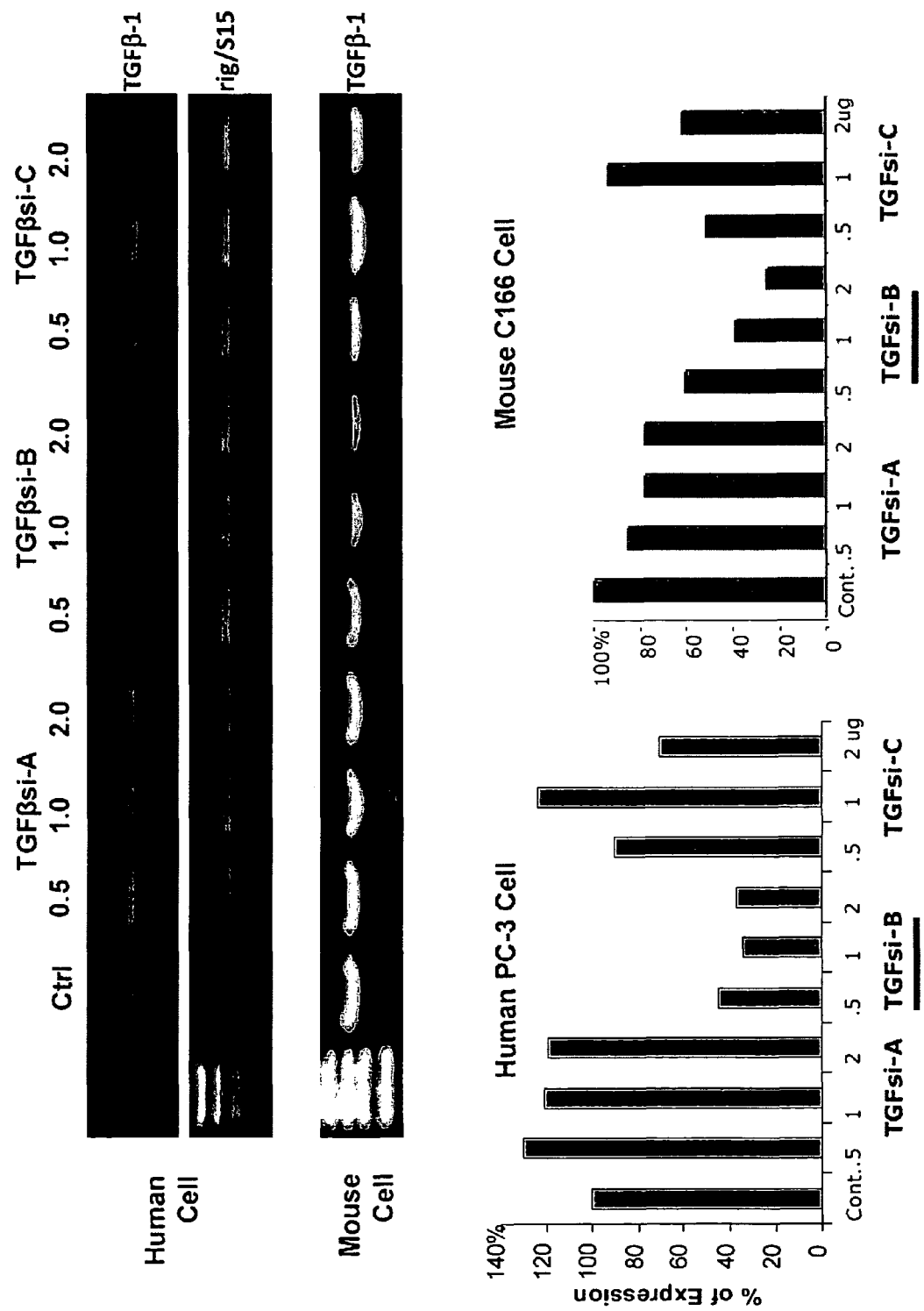

FIG. 10. RT-PCR analysis for selection of potent siRNA targeting TGFβ1 The silencing activities of three siRNA oligos targeting the TGFβ-1 gene expression was demonstrated through gel electrophoresis analysis. A potent siRNA oligo was identified based on the silencing activities in both human and moue cells. hmTGFβ1: sense, 5'-CCCAAGGGCUAC-CAUGCCAACUUCU-3' (SEQ ID NO: 7), antisense, 5'-AGAAGUUGGCAUGGUAGCCCUUGGG-3' (SEQ ID NO: 8).

Figure 11:
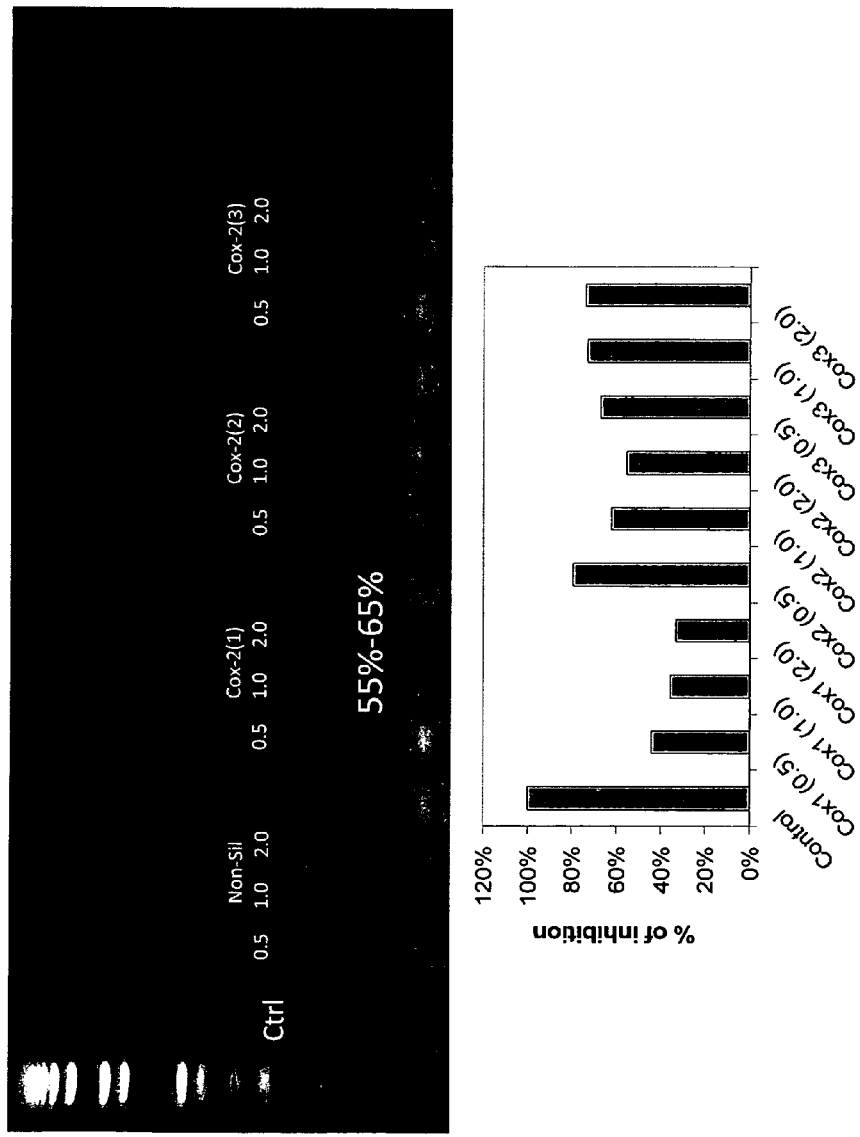

FIG. 11. RT-PCR analysis for selection of potent siRNA targeting Cox-2 The silencing activities of three siRNA oligos targeting the Cox-2 gene expression was demonstrated through gel electrophoresis analysis. A potent siRNA oligo was identified based on the silencing activities in both human and mouse cells. hmCox-2: sense, 5'-GGUCUGGUGCCUG-GUCUGAUGAUGU-3' (SEQ ID NO: 6), antisense, 5'-ACAUCAUCAGACCAGGCACCAGACC-3' (SEQ ID NO: 9).

Figure 12:
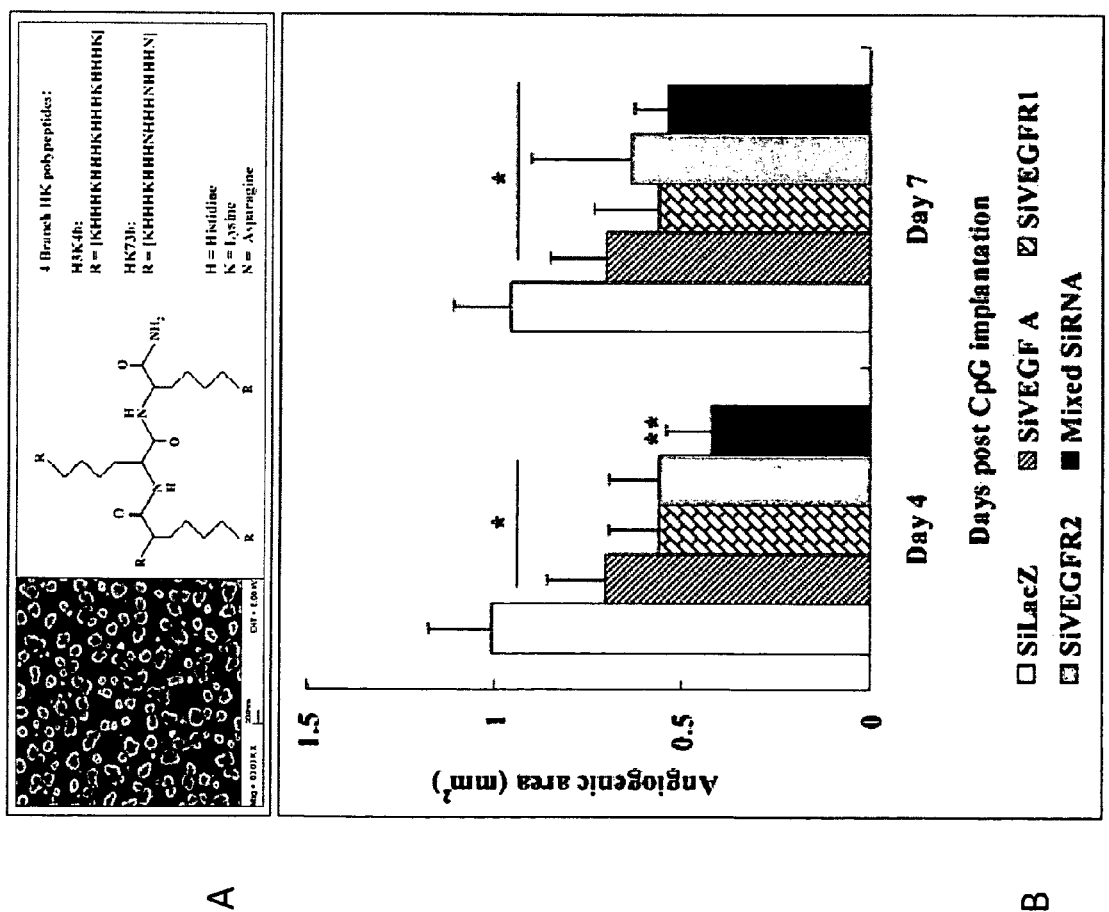

FIG. 12. HKP for in vivo siRNA Delivery (A) Polymeric Nanoparticle-siRNA Systems Histidine-Lysine polymer (HKP) mixed with siRNA duplexes resulted in HKP-siRNA nanoparticles. Structures of two species of HKP, H3K4b and PT73, were showed with the scanning electron microscope (SEM) image of HKP-siRNA nanoparticle. FIG. 12A discloses SEQ ID NOS 255-256, respectively, in order of appearance. (B) Cocktail siRNAs are more potent than single siRNA for anti-angiogenesis efficacy of siRNA cocktail on ocular NV. Local delivery of HKP-siRNA cocktail (black bar) significantly minimized angiogenesis areas in mouse eyes at P4 (**P<0.01, n=8) compared to single gene targeted HKP-siRNA: VEGF (grey), VEGFR1 and VEGFR2 (stripe and dot) at P4 ((*P<0.05). At P7, VEGF and VEGFR1 specific siRNA lost the inhibitory activities, while the cocktail siRNA are still demonstrated its activity.

Figure 13:
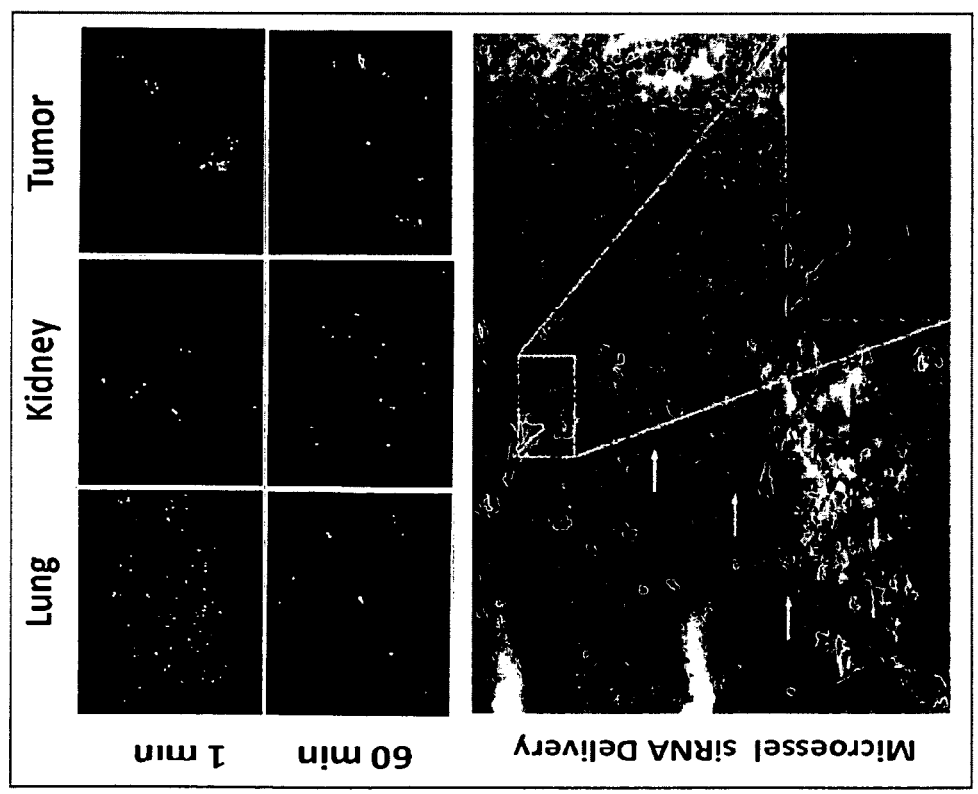

FIG. 13. HKP for Systemic Tumor siRNA Delivery Accumulation of intravenously (IV) delivered HKP-encapsulated siRNA molecules in established head and neck squamous cancer 1483 xenograft tumors. A: Images of mouse tissues and tumors with Alexa Fluor 555 labeled fluorescent siRNA CT-2 deposits following tail vein injection of HKP-siRNA. The tissues were harvested at the indicated time, freshly frozen, sectioned, and analyzed by fluorescent microscopy. Magnification: 400×. B: Accumulation of fluorescent CT-2 (Red deposits indicated with arrows) in the tumors in proximity to blood vessels (Brown; CD31 immunostaining). Magnification: 400×. Inset: Detail showing labeled siRNA in tumor tissue.

DETAILED DESCRIPTION OF THE INVENTION

The invention provides siRNA molecules, compositions containing the molecules, and methods of using the compositions to treat a glioma in a subject. As used herein, an "siRNA molecule" is a duplex oligonucleotide, that is a short, double-stranded oligonucleotide, that interferes with the expression of a gene in a cell that produces RNA, after the molecule is introduced into the cell. Such molecules are constructed by techniques known to those skilled in the art. Such techniques are described in U.S. Pat. Nos. 5,898,031, 6,107,094, 6,506,559, 7,056,704 and in European Pat. Nos. 1214945 and 1230375, which are incorporated herein by reference in their entireties.

The siRNA molecule of the invention is an isolated siRNA molecule that binds to a single stranded RNA molecule, which is a messenger RNA (mRNA) that encodes at least part of a peptide or protein whose activity promotes tumorigenesis, angiogenesis, or cell proliferation in the brain or spinal cord of a mammal, or which is a micro-RNA (miRNA) whose activity promotes tumorigenesis, angiogenesis, or cell proliferation in the brain or spinal cord of a mammal. In one embodiment, the molecule is an oligonucleotide with a length of about 19 to about 35 base pairs. In another embodiment, the molecule is an oligonucleotide with a length of about 19 to about 27 base pairs. In still another embodiment, the molecule is an oligonucleotide with a length of about 21 to about 25 base pairs. In all of these embodiments, the molecule may have blunt ends at both ends, or sticky ends at both ends, or a blunt end at one end and a sticky end at the other.

The siRNA molecule can be made of naturally occurring ribonucleotides, i.e., those found in living cells, or one or more of its nucleotides can be chemically modified by techniques known in the art. In addition to being modified at the level of one or more of its individual nucleotides, the backbone of the oligonucleotide also can be modified. Additional modifications include the use of small molecules (e.g. sugar molecules), amino acid molecules, peptides, cholesterol and other large molecules for conjugation onto the siRNA molecules.

In one embodiment, the siRNA molecule binds to an mRNA that encodes at least part of a peptide or protein whose activity promotes tumorigenesis, angiogenesis, or cell proliferation in the brain or spinal cord of a mammal. Such may be the case when the mRNA molecule encodes a protein in a pro-tumorigenic pathway, pro-angiogenesis pathway, pro-cell proliferation pathway, or anti-apoptotic pathway. For example, the protein can be a VEGF pathway protein, EGFR pathway protein, MGMT pathway protein, RAF pathway protein, MMP pathway protein, mTOR pathway protein, TGFβ pathway protein, or Cox-2 pathway protein. In one embodiment, the protein is one of the following: VEGF, EGFR, PI3K, AKT, AGT, RAF1, RAS, MAPK, ERK, MGMT, MMP-2, MMP-9, PDGF, PDGFR, IGF-1, HGF, mTOR, Cox-2, or TGFβ1. In another embodiment, the protein is VEGF, EGFR, MGMT, MMP-2, MMP-9, or PDGF. In still another embodiment, the protein is RAF1, mTOR, Cox-2, or TGFβ1.

In one embodiment, the siRNA molecule binds to both a human mRNA molecule and a homologous mouse mRNA molecule. That is, the human and mouse mRNA molecules encode proteins that are substantially the same in structure or function. Therefore, the efficacy and toxicity reactions observed in the mouse disease models (e.g. tumor models) will allow us to have a good understanding about what is going to happen in humans. More importantly, the siRNA molecules tested in the mouse model are good candidates for human pharmaceutical agents. The human/mouse homology design of an siRNA drug agent can eliminate the toxicity and adverse effect of those species specificities observed in monoclonal antibody drugs.

In another embodiment, the siRNA molecule binds to an miRNA whose activity promotes tumorigenesis, angiogenesis, or cell proliferation in the brain or spinal cord of a mammal. As used herein, an miRNA is a short, single-stranded RNA molecule that down-regulates gene expression through a loose homology binding to the 3' end of the untranslated region of a particular gene target. Such molecules are transcribed from DNA, but are not translated into a polypeptide. It has been associated with certain diseases (e.g. glioblastoma).

Similarly, siRNA molecules can be designed to bind to other single-stranded RNA molecules that can regulate gene expression through mechanisms other than the RNAi effect.

The siRNA molecules of the invention are used to treat one or more gliomas in the brain or spinal cord of a subject. In practice, a plurality of the molecules are used. The siRNA molecules may bind to a peptide or protein that causes or promotes the growth of a glioma in the subject. In one embodiment, the subject is a mammal, such as a mouse, non-human primate, or human. In another embodiment, the subject is a human. In one embodiment, the glioma is an astrocytoma. In another embodiment, it is a type of astrocytoma known as a glioblastoma multiforme (GBM). The molecules are delivered to the subject in pharmaceutically acceptable carriers known to those skilled in the by techniques known to those skilled in the art.

The invention also includes compositions of a plurality of the siRNA molecules, where each one targets a different RNA nucleotide sequence, which can be on the same RNA target molecule, different RNA target molecules, or any combination thereof. These compositions, in combination with pharmaceutically acceptable carriers, such as those described herein, are sometimes called siRNA cocktails. Thus, the invention provides multi-targeted siRNA cocktails for the treatment of gliomas.

All possible combinations of types of molecules and targets are included in the invention. For example, the targeted RNA molecules may encode or regulate the expression of one or more proteins in the subject. The proteins can be in the same or different pathways. The pathways, categories of proteins, and specific proteins are the ones identified previously herein. In one embodiment, the composition comprises two or more different siRNA molecules, each binding to a different RNA target sequence. In another embodiment, the composition comprises three different siRNA molecules, each binding to a different RNA target sequence. In still another embodiment, the composition comprises more than three different siRNA molecules, each binding to a different RNA target sequence. In one embodiment, the siRNA molecules target one or more of the mRNA molecules that are transcribed from one or more of the gene sequences listed in Tables 1-6 herein. In another embodiment, the siRNA molecules are selected from those listed in Tables 7-12 herein.

In yet another embodiment, the composition comprises at least one siRNA (sense: 5'-CUGUAGACACACCCACCCA-CAUACA-3' (SEQ ID NO: 10), antisense: 5'-UGUAU-GUGGGUGGGUGUGUCUACAG-3' (SEQ ID NO: 11)) or (sense 5'-CCCUGGUGGACAUCUUCCAGGAGUA-3' (SEQ ID NO: 12), antisense 5'-UACUCCUGGAA-GAUGUCCACCAGGG-3' (SEQ ID NO: 13)) that binds to an mRNA molecule that encodes both a human and a mouse VEGF protein, at least one siRNA molecule (sense: 5'-CCAUCGAUGUCUACAUGAUCAUGGU-3' (SEQ ID NO: 14), antisense: 5'-ACCAUGAUCAUGUAGACAUC-GAUGG-3' (SEQ ID NO: 15)) or (sense 5'-GAUCAUGGU-CAAGUGCUGGAUGAUA-3' (SEQ ID NO: 16), antisense 5'-UAUCAUCCAGCACUUGACCAUGAUC-3' (SEQ ID NO: 17)) that binds to an mRNA molecule that encodes both a human and mouse EGFR protein, and at least one siRNA molecule (sense: 5'-GCUGAAGGUUGUGAAAUUCG-GAGAA-3' (SEQ ID NO: 18), antisense: 5'-UUCUC-CGAAUUUCACAACCUUCAGC-3' (SEQ ID NO: 19)) or (sense 5'-GCUGCUGAAGGUUGUGAAAUUCGGA-3' (SEQ ID NO: 20), antisense 5'-UCCGAAUUUCACAAC-CUUCAGCAGC-3' (SEQ ID NO: 21)) that binds to an mRNA molecule that encodes both a human and mouse MGMT protein.

As previously mentioned, the siRNA cocktails of the invention comprise two or more different siRNA molecules of the invention in a pharmaceutically acceptable carrier. Such carriers are generally known to those skilled in the art and include saline, sugars, polypeptides, polymers, lipids, creams, gels, micelle materials, and metal nanoparticles. In one embodiment, the carrier comprises at least one of the following: a glucose solution, a polycationic binding agent, a cationic lipid, a cationic micelle, a cationic polypeptide, a hydrophilic polymer grafted polymer, a non-natural cationic polymer, a cationic polyacetal, a hydrophilic polymer grafted polyacetal, a ligand functionalized cationic polymer, a ligand functionalized-hydrophilic polymer grafted polymer, and a ligand functionalized liposome. In another embodiment, the polymers comprise a biodegradable histidine-lysine polymer, a biodegradable polyester, such as poly(lactic acid) (PLA), poly(glycolic acid) (PGA), and poly(lactic-co-glycolic acid) (PLGA), a polyamidoamine (PAMAM) dendrimer, a cationic lipid (such as DOTAP), or a PEGylated PEI. In still another embodiment, the carrier is a histidine-lysine copolymer that forms a nanoparticle with the siRNA molecule, wherein the diameter of the nanoparticle is about 100 nm to about 500 nm. In a further embodiment, the ligand comprises one or more of an RGD peptide, such as H-ACRGDMFGCA-OH, an RVG peptide, such as H-YTIWMPENPRPGTPCDIFT-NSRGKRASNG-OH, or a FROP peptide, such as H-EDYELMDLLAYL-OH.

The invention also provides a nanoparticle comprising the siRNA molecule of the invention, a carrier, such as one or more of those described herein, and a targeting ligand. Examples of targeting ligands include EGF receptor ligands, IL13 ligand, hepatocyte growth factor ligand, single chain monoclonal antibodies, RGD peptide ligands, and RVG peptide ligands. In one embodiment, the nanoparticle comprises an RGD peptide ligand. In another embodiment, it comprises an RVG peptide ligand.

These nanoparticles may be used to prepare the siRNA cocktails previously described herein. Thus, the invention also includes a composition comprising 3 or more of the nanoparticles described herein.

The invention also provides a method of treating a subject with a glioma by administering to the subject an effective amount of one or more of the siRNA molecules of the invention or the compositions of the invention. The subject is a mammal. In one embodiment, the mammal is a mouse or rat. In another embodiment, it is a non-human primate. In another embodiment, the subject is a human patient. The glioma may be characterized at least in part by neovascularization and inflammation in the subject's brain or spinal cord. In one embodiment, the glioma is an astrocytoma. In another embodiment, the astrocytoma is a glioblastome multiforme.

The compositions are administered by techniques known to those skilled in the art. In one embodiment, the composition comprises at least three siRNA molecules at a ratio determined by the potency of each siRNA molecule and the therapeutic needs of the subject. In another embodiment, the composition comprises three different siRNA molecules at a ratio of 1:1:1, 1:1.5:0.5, or 0.5:0.5:2.

The compositions of the invention can be used with an effective amount of other anti-cancer therapeutic agents. These include ones that impede or block tumorigenesis, angiogenesis, or cell proliferation in the brain or spinal cord of a mammal. In one embodiment, the agent impedes or blocks the activity of a peptide or protein whose activity promotes tumorigenesis, angiogenesis, or cell proliferation in the brain or spinal cord of the mammal. For example, it may impede or block the activity of a peptide or protein that causes or promotes the growth of a glioma. In one embodiment, it impedes or blocks the activity of a protein that is a pro-tumorigenic pathway protein, a pro-angiogenesis pathway protein, a pro-cell proliferation pathway protein, or an anti-apoptotic pathway protein. Such proteins include, but are not limited to, a VEGF pathway protein, EGFR pathway protein, MGMT pathway protein, RAF pathway protein, MMP pathway protein, mTOR pathway protein, TGFβ pathway protein, or Cox-2 pathway protein. Particular examples of proteins that may be targeted by the therapeutic agent are VEGF, EGFR, PI3K, AKT, RAF1, RAS, MAPK, ERK, MGMT, MMP-2, MMP-9, PDGF, PDGFR, IGF-1, HGF, mTOR, Cox-2, and TGFβ.

In one embodiment of the invention, the therapeutic agent is selected from the group consisting of bevacizumab (trade name Avastin), sunitinib (trade name Sutent), sorafenib (trade name Nexavar), temsirolimus (trade name Torisel), and temozolomide (trade name Temodar). In one embodiment, a composition of the invention comprises temozolomide and siRNA molecules that inhibit the expression of MGMT and two of the following: EGFR, VEGF, PDFG, MMP-2, and MMP-9. In another embodiment, a composition of the invention comprises bevacizumab and siRNA molecules that inhibit the expression of two of the following: EGFR, PDFG, MMP-2, and MMP-9. In still another embodiment, a composition of the invention comprises temozolomide and siRNA molecules that inhibit the expression of EGFR, VEGF, and MGMT.

EXAMPLES

The following examples illustrate certain aspects and embodiments of the invention and should not be construed as limiting the scope thereof.

Designing siRNA Inhibitors

Our experimental approach provides a novel approach to designing siRNA targeting sequences. It differs from other approaches in three important aspects:

(1) The sequences designed to be targeted by siRNA duplexes have homology to both human and mouse sequences of the same gene. That means that each of the designed siRNA duplexes will be able to knock down the same gene target in either human or mouse cells. For example, a potent siRNA specific to the VEGF gene will be able to knock down both human VEGF and mouse VEGF gene expression.

(2) The sequences were designed in three different lengths: 21-mer, 23-mer, and 25-mer. One consideration is that 23-mer and 25-mer are usually more potent than 21-mer siRNA, but 25-mer may have a greater potential for inducing an unwanted interferon response. Therefore, siRNA duplexes at various lengths may provide the best chance to achieve potent inhibition with less interferon response.

(3) The siRNA oligos can be obtained in either blunt end or sticky end form, according to the synthesis design and annealing. One consideration is that the sticky end siRNA oligos may be sensitive to degradation, and the blunt end siRNA oligos may activate the cellular interferon response.

As used herein, "oligonucleotides" and similar terms relate to short oligos composed of naturally occurring nucleotides as well as to oligos composed of synthetic or modified nucleotides, as described in the preceding section on RNAi and siRNA. The terms "polynucleotide" and "oligonucleotide" are used synonymously.

Design of siRNA Sequences Against Targets

Tables 1-6 present the sequences of six genes targeted by specific siRNA sequences. To identify the most potent siRNA duplex targeting three of these genes, EGFR, VEGF, and MGMT, we generated EGFR, VEGF, and MGMT siRNAs and evaluated the effect of siRNA-mediated gene knockdown in vitro. They provide templates for the design of specific siRNAs.

TABLE 1

The targeted sequences of VEGF-A gene of both human and mouse

| Organism | Gene | homology | Length | No. | Sense Sequences | SEQ ID NO: |
|---|---|---|---|---|---|---|
| Human Mouse | VEGF165 | Human Mouse | 21-mer | 1 | gtgtgcgcagacagtgctcca | 25 |
| | | | | 2 | ccaccatgccaagtggtccca | 26 |
| | | | | 3 | cctggtggacatcttccagga | 27 |
| | | | | 4 | gcacataggagagatgagctt | 28 |
| | | | | 5 | caagatccgcagacgtgtaaa | 29 |
| | | | | 6 | ggcgaggcagcttgagttaaa | 30 |
| | | | | 7 | cttgagttaaacgaacgtact | 31 |
| | | | | 8 | ggaaggagcctccctcagggt | 32 |
| | | | | 9 | cactttgggtccggagggcga | 33 |
| | | | | 10 | cagtattcttggttaatattt | 34 |
| | | | 23-mer | 1 | gcctccgaaaccatgaactttct | 35 |
| | | | | 2 | ctccaccatgccaagtggtccca | 36 |
| | | | | 3 | cctggtggacatcttccaggagt | 37 |
| | | | | 4 | cagcacataggagagatgagctt | 38 |
| | | | | 5 | gcttgagttaaacgaacgtactt | 39 |
| | | | | 6 | gttaaacgaacgtacttgcagat | 40 |
| | | | | 7 | ggaaggagcctccctcagggttt | 41 |
| | | | | 8 | ctccctcagggtttcgggaacca | 42 |
| | | | | 9 | ctaatgttattggtgtcttcact | 43 |
| | | | | 10 | gagaaagtgttttatatacggta | 44 |
| | | | 25-mer | 1 | cctccgaaaccatgaactttctgct | 45 |
| | | | | 2 | ccaccatgccaagtggtcccaggct | 46 |
| | | | | 3 | ccctggtggacatcttccaggagta | 47 |
| | | | | 4 | gatccgcagacgtgtaaatgttcct | 48 |
| | | | | 5 | cgcagacgtgtaaatgttcctgcaa | 49 |
| | | | | 6 | gtaaatgttcctgcaaaaacacaga | 50 |
| | | | | 7 | cagcttgagttaaacgaacgtactt | 51 |
| | | | | 8 | gttaaacgaacgtacttgcagatgt | 52 |
| | | | | 9 | ccatgccaagtggtcccaggctgca | 53 |
| | | | | 10 | ccctggtggacatcttccaggagta | 47 |

TABLE 2

The targeted sequences of EGFR gene of both human and mouse

| Organism | Gene | homology | Length | No. | Sense Sequences | SEQ ID NO: |
|---|---|---|---|---|---|---|
| Human Mouse | EGFR | Human Mouse | 21-mer | 1 | ccctgactaccagcaggactt | 54 |
| | | | | 2 | ctgactaccagcaggacttct | 55 |
| | | | | 3 | caggggatgaaagaatgcat | 56 |
| | | | | 4 | gggggatgaaagaatgcattt | 57 |
| | | | | 5 | gaattctccaaaatggcccga | 58 |
| | | | | 6 | ccatcgatgtctacatgatca | 59 |

TABLE 2-continued

The targeted sequences of EGFR gene of both human and mouse

| Organism | Gene | homology | Length | No. | Sense Sequences | SEQ ID NO: |
|---|---|---|---|---|---|---|
| | | | | 7 | gatcatggtcaagtgctggat | 60 |
| | | | | 8 | cgatgtctacatgatcatggt | 61 |
| | | | | 9 | caaagtgcctatcaagtggat | 62 |
| | | | | 10 | ctggatcccagaaggtgagaa | 63 |
| | | | 23-mer | 1 | gacaaccctgactaccagcagga | 64 |
| | | | | 2 | caaccctgactaccagcaggact | 65 |
| | | | | 3 | ccctgactaccagcaggacttct | 66 |
| | | | | 4 | caggggatgaaagaatgcattt | 67 |
| | | | | 5 | ggatgaaagaatgcatttgccaa | 68 |
| | | | | 6 | gaattctccaaaatggcccgaga | 69 |
| | | | | 7 | cgatgtctacatgatcatggtca | 70 |
| | | | | 8 | ctacatgatcatggtcaagtgct | 71 |
| | | | | 9 | ggcaaagtgcctatcaagtggat | 72 |
| | | | | 10 | ctctggatcccagaaggtgagaa | 73 |
| | | | 25-mer | 1 | gacaaccctgactaccagcaggact | 74 |
| | | | | 2 | ggggatgaaagaatgcatttgccaa | 75 |
| | | | | 3 | ccatcgatgtctacatgatcatggt | 76 |
| | | | | 4 | gatgtctacatgatcatggtcaagt | 77 |
| | | | | 5 | gtctacatgatcatggtcaagtgct | 78 |
| | | | | 6 | gatcatggtcaagtgctggatgata | 79 |
| | | | | 7 | gatcacagattttgggctggccaaa | 80 |
| | | | | 8 | cagattttgggctggccaaactgct | 81 |
| | | | | 9 | cacagattttgggctggccaaactg | 82 |
| | | | | 10 | ctctggatcccagaaggtgagaaag | 83 |

TABLE 3

The targeted sequences of MGMT gene of both human and mouse

| Organism | Gene | homology | Length | No. | Sense Sequences | SEQ ID NO: |
|---|---|---|---|---|---|---|
| Human Mouse | MGMT | Human Mouse | 21-mer | 1 | caccagacaggtgttatggaa | 84 |
| | | | | 2 | cagacaggtgttatggaagct | 85 |
| | | | | 3 | ggtgttatggaagctgctgaa | 86 |
| | | | | 4 | ggaagctgctgaaggttgtga | 87 |
| | | | | 5 | gctgctgaaggttgtgaaatt | 88 |
| | | | | 6 | gaaggttgtgaaattcggaga | 89 |
| | | | | 7 | cagcaattagcagccctggca | 90 |
| | | | | 8 | cagcaattagcagccctggca | 90 |
| | | | | 9 | cagccctggcaggcaaccca | 91 |
| | | | | 10 | gccctggcaggcaaccccaaa | 92 |
| | | | 23-mer | 1 | ccagacaggtgttatggaagct | 93 |
| | | | | 2 | gacaggtgttatggaagctgct | 94 |
| | | | | 3 | caggtgttatggaagctgctga | 95 |
| | | | | 4 | gttatggaagctgctgaaggtt | 96 |
| | | | | 5 | ggaagctgctgaaggttgtgaa | 97 |
| | | | | 6 | gctgaaggttgtgaaattcgga | 98 |
| | | | | 7 | gaaggttgtgaaattcggagaa | 99 |
| | | | | 8 | cttaccagcaattagcagccct | 100 |
| | | | | 9 | ccagcaattagcagccctggca | 101 |
| | | | | 10 | gcagccctggcaggcaacccca | 102 |
| | | | 25-mer | 1 | ccagacagguguuauggaagcugcu | 103 |
| | | | | 2 | gacagguguuauggaagcugcugaa | 104 |
| | | | | 3 | gguguuauggaagcugcugaagguu | 105 |
| | | | | 4 | ggaagcugcugaagguugugaaauu | 106 |
| | | | | 5 | gcugcugaagguugugaaauucgga | 20 |
| | | | | 6 | gcugaagguugugaaauucggagaa | 18 |
| | | | | 7 | cagcaauuagcagcccuggcaggca | 107 |
| | | | | 8 | cuuaccagcaauuagcagcccuggc | 108 |
| | | | | 9 | ccagcaauuagcagcccuggcaggc | 109 |
| | | | | 10 | gcaauuagcagcccuggcaggcaac | 110 |

TABLE 4

The targeted sequences of MMP-2 gene of both human and mouse

| Organism | Gene | homology | Length | No. | Sense Sequences | SEQ ID NO: |
|---|---|---|---|---|---|---|
| Human Mouse | MMP-2 | Human Mouse | 21-mer | 1 | cccttgtttccgctgcatcca | 111 |
| | | | | 2 | catcatcaagttccccggcga | 112 |
| | | | | 3 | gacaaagagttggcagtgcaa | 113 |

TABLE 4-continued

The targeted sequences of MMP-2 gene of both human and mouse

| | | | SEQ ID NO: |
|---|---|---|---|
| | 4 | gcaacccagatgtggccaact | 114 |
| | 5 | caagcccaagtgggacaagaa | 115 |
| | 6 | gcccaagtgggacaagaacca | 116 |
| | 7 | caactttgagaaggatggcaa | 117 |
| | 8 | gatggcatcgctcagatccgt | 118 |
| | 9 | cctggatgccgtcgtggacct | 119 |
| | | gccagggatctcttcaatgct | 120 |
| 23-mer | 1 | cccttgtttccgctgcatccaga | 121 |
| | 2 | ccatcatcaagttccccggcgat | 122 |
| | 3 | gacaaagagttggcagtgcaata | 123 |
| | 4 | ggcaacccagatgtggccaacta | 124 |
| | 5 | cgcaagcccaagtgggacaagaa | 125 |
| | 6 | gcccaagtgggacaagaaccaga | 126 |
| | 7 | ggacaagaaccagatcacataca | 127 |
| | 8 | caactttgagaaggatggcaagt | 128 |
| | 9 | ggcatcgctcagatccgtggtga | 129 |
| | 10 | ctggatgccgtcgtggacctgca | 130 |
| 25-mer | 1 | cccttgtttccgctgcatccagact | 131 |
| | 2 | ccatcatcaagttccccggcgatgt | 132 |
| | 3 | gagttggcagtgcaatacctgaaca | 133 |
| | 4 | gcaacccagatgtggccaactacaa | 134 |
| | 5 | gcaagcccaagtgggacaagaacca | 135 |
| | 6 | cccaagtgggacaagaaccagatca | 136 |
| | 7 | gacaagaaccagatcacatacagga | 137 |
| | 8 | ggcatcgctcagatccgtggtgaga | 138 |
| | 9 | gagcgtgaagtttggaagcatcaaa | 139 |
| | 10 | gagatcttcttcttcaaggaccggt | 140 |

TABLE 5

The targeted sequences of MMP-9 gene of both human and mouse

| Organism | Gene | homology | Length | No. | Sense Sequences | SEQ ID NO: |
|---|---|---|---|---|---|---|
| Human Mouse | MMP-9 | Human Mouse | 21-mer | 1 | catccagtttggtgtcgcgga | 141 |
| | | | | 2 | ccagtttggtgtcgcggagca | 142 |
| | | | | 3 | gcggagcacggagacgggtat | 143 |
| | | | | 4 | cggagacgggtatcccttcga | 144 |
| | | | | 5 | gagctgtgcgtcttcccttc | 145 |
| | | | 23-mer | 1 | gtcatccagtttggtgtcgcgga | 146 |
| | | | | 2 | gcgcggagcacggagacgggtat | 147 |
| | | | | 3 | ggagcacggagacgggtatccct | 148 |
| | | | 25-mer | 1 | ccagtttggtgtcgcggagcacgga | 149 |
| | | | | 2 | cgcgcgcggagcacggagacgggta | 150 |
| | | | | 3 | cggagcacggagacgggtatccctt | 151 |
| | | Human only s: sense a: antisense | 21-mer | 1s | CCACCACAACAUCACCUAUTT | 152 |
| | | | | 1a | AUAGGUGAUGUUGUGGUGGTT | 153 |
| | | | | 2s | GCCAGUUUCCAUUCAUCUUTT | 154 |
| | | | | 2a | AAGAUGAAUGGAAACUGGCTT | 155 |
| | | | | 3s | GCGCUGGGCUUAGAUCAUUTT | 156 |
| | | | | 3a | AAUGAUCUAAGCCCAGCGCTT | 157 |
| | | | | 4s | GCAUAAGGACGACGUGAAUTT | 158 |
| | | | | 4a | AUUCACGUCGUCCUUAUGCTT | 159 |
| | | | | 5s | CCUGCAACGUGAACAUCUUTT | 160 |
| | | | | 5a | AAGAUGUUCACGUUGCAGGTT | 161 |
| | | | | 6s | GGAACCAGCUGUAUUUGUUTT | 162 |
| | | | | 6a | AACAAAUACAGCUGGUUCCTT | 163 |
| | | | | 7s | GCCAGUUUGCCGGAUACAATT | 164 |
| | | | | 7a | UUGUAUCCGGCAAACUGGCTT | 165 |
| | | | | 8s | CCAGUUUGCCGGAUACAAATT | 166 |
| | | | | 8a | UUUGUAUCCGGCAAACUGGTT | 167 |
| | | | | 9s | GCCGGAUACAAACUGGUAUTT | 168 |
| | | | | 9a | AUACCAGUUUGUAUCCGGCTT | 169 |
| | | | | 10s | CCGGAUACAAACUGGUAUUTT | 170 |
| | | | | 10a | AAUACCAGUUUGUAUCCGGTT | 171 |
| | | Human only s: sense a: antisense | 25-mer | 1s | UGGCACCACCACAACAUCACCUAUU | 172 |
| | | | | 1a | AAUAGGUGAUGUUGUGGUGGUGCCA | 173 |
| | | | | 2s | CACAACAUCACCUAUUGGAUCCAAA | 174 |
| | | | | 2a | UUUGGAUCCAAUAGGUGAUGUUGUG | 175 |
| | | | | 3s | GACGCAGACAUCGUCAUCCAGUUUG | 176 |
| | | | | 3a | CAAACUGGAUGACGAUGUCUGCGUC | 177 |
| | | | | 4s | GGAAACCCUGCCAGUUUCCAUUCAU | 178 |
| | | | | 4a | AUGAAUGGAAACUGGCAGGGUUUCC | 179 |

TABLE 5-continued

The targeted sequences of MMP-9 gene of both human and mouse

| Organism | Gene | homology | Length | No. | Sense Sequences | SEQ ID NO: |
|---|---|---|---|---|---|---|
| | | | | 5s | CAUUCAUCUUCCAAGGCCAAUCCUA | 180 |
| | | | | 5a | UAGGAUUGGCCUUGGAAGAUGAAUG | 181 |
| | | | | 6s | ACGAUGCCUGCAACGUGAACAUCUU | 182 |
| | | | | 6a | AAGAUGUUCACGUUGCAGGCAUCGU | 183 |
| | | | | 7s | GCGGAGAUUGGGAACCAGCUGUAUU | 184 |
| | | | | 7a | AAUACAGCUGGUUCCCAAUCUCCGC | 185 |
| | | | | 8s | CGGAGAUUGGGAACCAGCUGUAUUU | 186 |
| | | | | 8a | AAAUACAGCUGGUUCCCAAUCUCCG | 187 |
| | | | | 9s | CAGUACCGAGAGAAAGCCUAUUUCU | 188 |
| | | | | 9a | AGAAAUAGGCUUUCUCUCGGUACUG | 189 |
| | | | | 10s | AAGCCUAUUUCUGCCAGGACCGCUU | 190 |
| | | | | 10a | AAGCGGUCCUGGCAGAAAUAGGCUU | 191 |

TABLE 6

The targeted sequences of PDGFa gene of both human and mouse

| Organism | Gene | homology | Length | No. | Sense Sequences | SEQ ID NO: |
|---|---|---|---|---|---|---|
| Human Mouse | PDGF a | Human Mouse | 21-mer | 1 | caccctcctccgggccgcgct | 192 |
| | | | | 2 | ctcctccgggccgcgctccct | 193 |
| | | | | 3 | gtactgaatttcgccgccaca | 194 |
| | | | | 4 | ctgaatttcgccgccacagga | 195 |
| | | | | 5 | ggagcgccgccccgcggcct | 196 |
| | | | | 6 | ctgctgctcctcggctgcgga | 197 |
| | | | | 7 | gctgctcctcggctgcggata | 198 |
| | | | | 8 | gatccacagcatccgggacct | 199 |
| | | | | 9 | ccacagcatccgggacctcca | 200 |
| | | | | 10 | catccgggacctccagcgact | 201 |
| | | | 23-mer | 1 | gccaccctcctccgggccgcgct | 202 |
| | | | | 2 | ccctcctccgggccgcgctccct | 203 |
| | | | | 3 | gatggtactgaatttcgccgcca | 204 |
| | | | | 4 | ctggagcgccgccccgcggcct | 205 |
| | | | | 5 | gcgcccgccccgcggcctcgcct | 206 |
| | | | | 6 | gcctcgggacgcgatgaggacct | 207 |
| | | | | 7 | ggcttgcctgctgctcctcggct | 208 |
| | | | | 8 | gcctgctgctcctcggctgcgga | 209 |
| | | | | 9 | cagatccacagcatccgggacct | 210 |
| | | | | 10 | gaccaggacggtcatttacgaga | 211 |
| | | | 25-mer | 1 | gcgccaccctcctccgggccgcgct | 212 |
| | | | | 2 | caccctcctccgggccgcgctccct | 213 |
| | | | | 3 | gggatggtactgaatttcgccgcca | 214 |
| | | | | 4 | gatggtactgaatttcgccgccaca | 215 |
| | | | | 5 | ggtactgaatttcgccgccacagga | 216 |
| | | | | 6 | ggctggagcgccgccccgcggcct | 217 |
| | | | | 7 | gagcgccgccccgcggcctcgcct | 218 |
| | | | | 8 | ccagcgcctcgggacgcgatgagga | 219 |
| | | | | 9 | gcgcctcgggacgcgatgaggacct | 220 |
| | | | | 10 | gcctgctgctcctcggctgcggata | 221 |

The following siRNA duplexes were designed to target human/mouse EGFR gene (BCER series, eight siRNAs), human/mouse VEGF gene (BCVF series, eight siRNAs) and human/mouse MGMT gene (MGMT series, eight siRNAs):

| BCER siRNA, siRNA duplexes targeting EGFR genes (both mouse and human), 25 mer blunt ended: | | |
|---|---|---|
| Sense: | 5'-CCAUCGAUGUCUACAUGAUCAUGGU-3' | (SEQ ID NO: 14) |
| Antisense: BCER-b | 5'-ACCAUGAUCAUGUAGACAUCGAUGG-3' | (SEQ ID NO: 15) |
| Sense: | 5'-GAUGUCUACAUGAUCAUGGUCAAGU-3' | (SEQ ID NO: 222) |
| Antisense: BCER-c: | 5'-ACUUGACCAUGAUCAUGUAGACAUC-3' | (SEQ ID NO: 223) |
| Sense: | 5'-GUCUACAUGAUCAUGGUCAAGUGCU-3' | (SEQ ID NO: 224) |
| Antisense: | 5'-AGCACUUGACCAUGAUCAUGUAGAC-3' | (SEQ ID NO: 225) |

-continued

BCER-d:

| | | |
|---|---|---|
| Sense: | 5'-GAUCAUGGUCAAGUGCUGGAUGAUA-3' | (SEQ ID NO: 16) |
| Antisense: | 5'-UAUCAUCCAGCACUUGACCAUGAUC-3' | (SEQ ID NO: 17) |

BCER-e:

| | | |
|---|---|---|
| Sense: | 5'-GAUCACAGAUUUUGGGCUGGCCAAA-3' | (SEQ ID NO: 226) |
| Antisense: | 5'-UUUGGCCAGCCCAAAAUCUGUGAUC-3' | (SEQ ID NO: 227) |

BCER-f:

| | | |
|---|---|---|
| Sense: | 5'-CAGAUUUUGGGCUGGCCAAACUGCU-3' | (SEQ ID NO: 228) |
| Antisense: | 5'-AGCAGUUUGGCCAGCCCAAAAUCUG-3' | (SEQ ID NO: 229) |

BCER-g:

| | | |
|---|---|---|
| Sense: | 5'-CACAGAUUUUGGGCUGGCCAAACUG-3' | (SEQ ID NO: 230) |
| Antisense: | 5'-CAGUUUGGCCAGCCCAAAAUCUGUG-3' | (SEQ ID NO: 231) |

BCER-h:

| | | |
|---|---|---|
| Sense: | 5'-CUCUGGAUCCCAGAAGGUGAGAAAG-3' | (SEQ ID NO: 232) |
| Antisense: | 5'-CUUUCUCACCUUCUGGGAUCCAGAG-3' | (SEQ ID NO: 233) |

BCVF siRNA, siRNA duplexes targeting VEGF gene (both mouse and human) 25 mer blunt ended:

BCVF-a

| | | |
|---|---|---|
| Sense: | 5'-CCAUGCCAAGUGGUCCCAGGCUGCA-3' | (SEQ ID NO: 234) |
| Antisense: | 5'-UGCAGCCUGGGACCACUUGGCAUGG-3' | (SEQ ID NO: 235) |

BCVF-b

| | | |
|---|---|---|
| Sense: | 5'-CCAACAUCACCAUGCAGAUUAUGCG-3' | (SEQ ID NO: 236) |
| Antisense: | 5'-CGCAUAAUCUGCAUGGUGAUGUUGG-3' | (SEQ ID NO: 237) |

BCVF-c

| | | |
|---|---|---|
| Sense: | 5'-CUGUAGACACACCCACCCACAUACA-3' | (SEQ ID NO: 10) |
| Antisense: | 5'-UGUAUGUGGGUGGGUGUGUCUACAG-3' | (SEQ ID NO: 11) |

BCVF-d

| | | |
|---|---|---|
| Sense: | 5'-CACUUUGGGUCCGGAGGGCGAGACU-3' | (SEQ ID NO: 238) |
| Antisense: | 5'-AGUCUCGCCCUCCGGACCCAAAGUG-3' | (SEQ ID NO: 239) |

BCVF-e

| | | |
|---|---|---|
| Sense: | 5'-CCAUGCCAAGUGGUCCCAGGCUGCA-3' | (SEQ ID NO: 234) |
| Antisense: | 5'-UGCAGCCUGGGACCACUUGGCAUGG-3' | (SEQ ID NO: 235) |

BCVF-f

| | | |
|---|---|---|
| Sense: | 5'-CCCUGGUGGACAUCUUCCAGGAGUA-3' | (SEQ ID NO: 12) |
| Antisense: | 5'-UACUCCUGGAAGAUGUCCACCAGGG-3' | (SEQ ID NO: 13) |

BCVF-g

| | | |
|---|---|---|
| Sense: | 5'-CGCAGACGUGUAAAUGUUCCUGCAA-3' | (SEQ ID NO: 240) |
| Antisense: | 5'-UUGCAGGAACAUUUACACGUCUGCG-3' | (SEQ ID NO: 241) |

BCVF-h

| | | |
|---|---|---|
| Sense: | 5'-CCCUGGUGGACAUCUUCCAGGAGUA-3' | (SEQ ID NO: 12) |
| Antisense: | 5'-UACUCCUGGAAGAUGUCCACCAGGG-3' | (SEQ ID NO: 13) |

BCMM siRNA, siRNA duplexes targeting MGMT gene (both human and mouse) 25 mer blunt ended:

BCMM-a:

| | | |
|---|---|---|
| Sense: | 5'-GGUGUUAUGGAAGCUGCUGAAGGUU-3' | (SEQ ID NO: 105) |
| Antisense: | 5'-AACCUUCAGCAGCUUCCAUAACACC-3' | (SEQ ID NO: 242) |

BCMM-b:

| | | |
|---|---|---|
| Sense: | 5'-GGAAGCUGCUGAAGGUUGUGAAAUU-3' | (SEQ ID NO: 106) |
| Antisense: | 5'-AAUUUCACAACCUUCAGCAGCUUCC-3' | (SEQ ID NO: 243) |

BCMM-c:

| | | |
|---|---|---|
| Sense: | 5'-GCUGCUGAAGGUUGUGAAAUUCGGA-3' | (SEQ ID NO: 20) |
| Antisense: | 5'-UCCGAAUUUCACAACCUUCAGCAGC-3' | (SEQ ID NO: 21) |

BCMM-d:

| | | |
|---|---|---|
| Sense: | 5'-GCUGAAGGUUGUGAAAUUCGGAGAA-3' | (SEQ ID NO: 18) |
| Antisense: | 5'-UUCUCCGAAUUUCACAACCUUCAGC-3' | (SEQ ID NO: 19) |

BCMM-e:

| | | |
|---|---|---|
| Sense: | 5'-CAGCAAUUAGCAGCCCUGGCAGGCA-3' | (SEQ ID NO: 107) |
| Antisense: | 5'-UGCCUGCCAGGGCUGCUAAUUGCUG-3' | (SEQ ID NO: 244) |

-continued

BCMM-f:

| | | |
|---|---|---|
| Sense: | 5'-CUUACCAGCAAUUAGCAGCCCUGGC-3' | (SEQ ID NO: 108) |
| Antisense: | 5'-GCCAGGGCUGCUAAUUGCUGGUAAG-3' | (SEQ ID NO: 245) |

BCMM-g:

| | | |
|---|---|---|
| Sense: | 5'-CCAGCAAUUAGCAGCCCUGGCAGGC-3' | (SEQ ID NO: 109) |
| Antisense: | 5'-GCCUGCCAGGGCUGCUAAUUGCUGG-3' | (SEQ ID NO: 246) |

BCMM-h:

| | | |
|---|---|---|
| Sense: | 5'-GCAAUUAGCAGCCCUGGCAGGCAAC-3' | (SEQ ID NO: 110) |
| Antisense: | 5'-GUUGCCUGCCAGGGCUGCUAAUUGC-3' | (SEQ ID NO: 247) |

Example I

Identification of the Most Potent siRNA Duplex Targeting the Above Three Genes to Demonstrate/Validate the Potency of siRNA Against Specific Target Genes To accomplish this objective, we generated EGFR, VEGF, and MGMT siRNAs and quantitatively evaluated the effect of siRNA-mediated gene knockdown in vitro using cell-culture-based assays. Gene knockdown was confirmed and evaluated by immunoblotting. We selected the most potent siRNA for each target gene for subsequent experiments. Using RT-PCR and Western blot analyses, we measured the gene expression silencing by each of the siRNA duplexes listed above, with optimized transfection followed by RNA and protein isolation. FIGS. 1-9 demonstrate the identified potent siRNA duplexes targeting each of the genes discussed.

Selection of Potent siRNA Sequences

A. Two siRNA duplexes were selected for MGMT knockdown:

MGMT-D

| | | |
|---|---|---|
| Sense | 5'-GCUGAAGGUUGUGAAAUUCGGAGAA-3' | (SEQ ID NO: 18) |
| Antisense | 5'-UUCUCCGAAUUUCACAACCUUCAGC-3' | (SEQ ID NO: 19) |

MGMT-C

| | | |
|---|---|---|
| Sense | 5'-GCUGCUGAAGGUUGUGAAAUUCGGA-3' | (SEQ ID NO: 20) |
| Antisense | 5'-UCCGAAUUUCACAACCUUCAGCAGC-3' | (SEQ ID NO: 21) |

B. Two siRNA duplexes were selected for EGFR knockdown:

EGFR-A

| | | |
|---|---|---|
| Sense | 5'-CCAUCGAUGUCUACAUGAUCAUGGU-3' | (SEQ ID NO: 14) |
| Antisense | 5'-ACCAUGAUCAUGUAGACAUCGAUGG-3' | (SEQ ID NO: 15) |

EGFR-D

| | | |
|---|---|---|
| Sense | 5'-GAUCAUGGUCAAGUGCUGGAUGAUA-3' | (SEQ ID NO: 16) |
| Antisense | 5'-UAUCAUCCAGCACUUGACCAUGAUC-3' | (SEQ ID NO: 17) |

C. Two siRNA duplexes were selected for human and mouse VEGF knockdown:

VEGF-C

| | | |
|---|---|---|
| Sense | 5'-CUGUAGACACACCCACCCACAUACA-3' | (SEQ ID NO: 10) |
| Antisense | 5'-UGUAUGUGGGUGGGUGUGUCUACAG-3' | (SEQ ID NO: 11) |

VEGF-H

| | | |
|---|---|---|
| Sense | 5'-CCCUGGUGGACAUCUUCCAGGAGUA-3' | (SEQ ID NO: 12) |
| Antisense | 5'-UACUCCUGGAAGAUGUCCACCAGGG-3' | (SEQ ID NO: 13) |

D. One siRNA duplex was selected for human and mouse PDGF knockdown:

hmPD-25-3:

| | | |
|---|---|---|
| sense: | 5'-GCCUGCUGCUCCUCGGCUGCGGAUA-3' | (SEQ ID NO: 5) |
| antisense: | 5'-UAUCCGCAGCCGAGGAGCAGCAGGC-3' | (SEQ ID NO: 248) |

E. One siRNA duplex was selected for human and mouse MMP-2 knockdown:

hmM2-25-3:

| | | |
|---|---|---|
| sense | 5'-CCCAAGUGGGACAAGAACCAGAUCA-3' | (SEQ ID NO: 249) |
| antisense | 5'-UGAUCUGGUUCUUGUCCCACUUGGG-3' | (SEQ ID NO: 250) |

F. One siRNA duplex was selected for human and mouse MMP-9 knockdown:

hmM9-25-1:

| | | |
|---|---|---|
| sense | 5'-CCAGUUUGGUGUCGCGGAGCACGGA-3' | (SEQ ID NO: 251) |
| antisense | 5'-UCCGUGCUCCGCGACACCAAACUGG-3' | (SEQ ID NO: 252) |

SiRNA Cocktail Therapeutics for GBM

We designed a therapeutic siRNA cocktail targeting multiple-disease controlling genes for treating several types of brain cancer, including GBM, acting on multiple aspects of the diseases and reducing potential toxicity.

The siRNA cocktail has the following characteristics:
(1) The siRNA cocktail contains at least three siRNA duplexes targeting at least three genes at a ratio required by the therapy.
(2) The cocktail design for each combination follows the understanding of the role of each gene in a background of the system biology network, such as whether these genes are functioning in the same pathway or in different ones.
(3) The chemical property of each siRNA molecule in the cocktail is the same in terms of source of supply, manufacturing process, chemical modification, storage conditions, and formulation procedures.
(4) The individual siRNA molecules in the cocktail can be of different lengths, with either blunt or sticky end, as long as their potencies have been defined.
(5) Since an siRNA cocktail is targeting multiple genes and a single cell type usually does not express all those factors, the efficacy of the siRNA cocktail is tested in a relevant disease model, either a multiple cell model, a tissue model, or an animal model, after confirmation of the potency of each individual siRNA duplex in the cell culture.
(6) Each validated siRNA cocktail can be used for addressing one or more pathological conditions or for treating one or multiple types of diseases, such as an siRNA cocktail for suppressing inflammation, siRNA cocktail for anti-angiogenesis activity and siRNA cocktail for autoimmune conditions.
(7) The siRNA cocktail is administrated through the same route of delivery in the same formulation, although the regimen of dosing for each cocktail will be defined based on either the experimental design or therapeutic requirements.
(8) Each siRNA cocktail can be applied either independently or in combination with other drug modalities, such as small molecule inhibitors, monoclonal antibodies, protein and peptides, and other siRNA cocktail drugs.

TABLE 7

VEGF-EGFR-MGMT siRNA cocktails
siRNA Cocktail Combinations (siRNA sense sequences)

| VEGF EGFR MGMT | | Human and Mouse homologues | SEQ ID NO: |
|---|---|---|---|
| Cocktail 1 | VEGF | 5'-CUGUAGACACACCCACCCACAUACA-3' | 10 |
| | EGFR | 5'-CCAUCGAUGUCUACAUGAUCAUGGU-3' | 14 |
| | MGMT | 5'-GCUGAAGGUUGUGAAAUUCGGAGAA-3' | 18 |
| Cocktail 2 | VEGF | 5'-CUGUAGACACACCCACCCACAUACA-3' | 10 |
| | EGFR | 5'-CCAUCGAUGUCUACAUGAUCAUGGU-3' | 14 |
| | MGMT | 5'-GCUGCUGAAGGUUGUGAAAUUCGGA-3' | 20 |
| Cocktail 3 | VEGF | 5'-CUGUAGACACACCCACCCACAUACA-3' | 10 |
| | EGFR | 5'-GAUCAUGGUCAAGUGCUGGAUGAUA-3' | 16 |
| | MGMT | 5'-GCUGCUGAAGGUUGUGAAAUUCGGA-3' | 20 |
| Cocktail 4 | VEGF | 5'-CCCUGGUGGACAUCUUCCAGGAGUA-3' | 12 |
| | EGFR | 5'-GAUCAUGGUCAAGUGCUGGAUGAUA-3' | 16 |
| | MGMT | 5'-GCUGCUGAAGGUUGUGAAAUUCGGA-3' | 20 |
| Cocktail 5 | VEGF | 5'-CCCUGGUGGACAUCUUCCAGGAGUA-3' | 12 |
| | EGFR | 5'-GAUCAUGGUCAAGUGCUGGAUGAUA-3' | 16 |
| | MGMT | 5'-GCUGAAGGUUGUGAAAUUCGGAGAA-3' | 18 |

TABLE 8

VEGF-EGFR-PDGF siRNA cocktails
siRNA Cocktail Combinations (siRNA sense sequences)

| VEGF EGFR PDGF | | Human and Mouse homologues | SEQ ID NO: |
|---|---|---|---|
| Cocktail 1 | VEGF | 5'-CUGUAGACACACCCACCCACAUACA-3' | 10 |
| | EGFR | 5'-CCAUCGAUGUCUACAUGAUCAUGGU-3' | 14 |
| | PDGF | 5'-GCCUGCUGCUCCUCGGCUGCGGAUA-3' | 5 |
| Cocktail 2 | VEGF | 5'-CCCUGGUGGACAUCUUCCAGGAGUA-3' | 12 |
| | EGFR | 5'-CCAUCGAUGUCUACAUGAUCAUGGU-3' | 14 |
| | PDGF | 5'-GCCUGCUGCUCCUCGGCUGCGGAUA-3' | 5 |
| Cocktail 3 | VEGF | 5'-CUGUAGACACACCCACCCACAUACA-3' | 10 |
| | EGFR | 5'-GAUCAUGGUCAAGUGCUGGAUGAUA-3' | 16 |
| | PDGF | 5'-GCCUGCUGCUCCUCGGCUGCGGAUA-3' | 5 |
| Cocktail 4 | VEGF | 5'-CCCUGGUGGACAUCUUCCAGGAGUA-3' | 12 |
| | EGFR | 5'-GAUCAUGGUCAAGUGCUGGAUGAUA-3' | 16 |
| | PDGF | 5'-GCCUGCUGCUCCUCGGCUGCGGAUA-3' | 5 |

TABLE 9

VEGF-EGFR-MMP-9 siRNA cocktails
siRNA Cocktail Combinations (siRNA sense sequences)

| VEGF EGFR MMP-9 | | Human and Mouse homologues | SEQ ID NO: |
|---|---|---|---|
| Cocktail 1 | VEGF | 5'-CUGUAGACACACCCACCCACAUACA-3' | 10 |
| | EGFR | 5'-CCAUCGAUGUCUACAUGAUCAUGGU-3' | 14 |
| | MMP-9 | 5'-CCAGUUUGGUGUCGCGGAGCACGGA-3' | 251 |
| Cocktail 2 | VEGF | 5'-CCCUGGUGGACAUCUUCCAGGAGUA-3' | 12 |
| | EGFR | 5'-CCAUCGAUGUCUACAUGAUCAUGGU-3' | 14 |
| | MMP-9 | 5'-CCAGUUUGGUGUCGCGGAGCACGGA-3' | 251 |
| Cocktail 3 | VEGF | 5'-CUGUAGACACACCCACCCACAUACA-3' | 10 |
| | EGFR | 5'-GAUCAUGGUCAAGUGCUGGAUGAUA-3' | 16 |
| | MMP-9 | 5'-CCAGUUUGGUGUCGCGGAGCACGGA-3' | 251 |
| Cocktail 4 | VEGF | 5'-CCCUGGUGGACAUCUUCCAGGAGUA-3' | 12 |
| | EGFR | 5'-GAUCAUGGUCAAGUGCUGGAUGAUA-3' | 16 |
| | MMP-9 | 5'-CCAGUUUGGUGUCGCGGAGCACGGA-3' | 251 |

TABLE 10

VEGF-EGFR-MMP-2 siRNA cocktails
siRNA Cocktail Combinations (siRNA sense sequences)

| VEGF EGFR MMP-2 | | Human and Mouse homologues | SEQ ID NO: |
|---|---|---|---|
| Cocktail 1 | VEGF | 5'-CUGUAGACACACCCACCCACAUACA-3' | 10 |
| | EGFR | 5'-CCAUCGAUGUCUACAUGAUCAUGGU-3' | 14 |
| | MMP-2 | 5'-CCCAAGUGGGACAAGAACCAGAUCA-3' | 249 |
| Cocktail 2 | VEGF | 5'-CCCUGGUGGACAUCUUCCAGGAGUA-3' | 12 |
| | EGFR | 5'-CCAUCGAUGUCUACAUGAUCAUGGU-3' | 14 |
| | MMP-2 | 5'-CCCAAGUGGGACAAGAACCAGAUCA-3' | 249 |
| Cocktail 3 | VEGF | 5'-CUGUAGACACACCCACCCACAUACA-3' | 10 |
| | EGFR | 5'-GAUCAUGGUCAAGUGCUGGAUGAUA-3' | 16 |
| | MMP-2 | 5'-CCCAAGUGGGACAAGAACCAGAUCA-3' | 249 |
| Cocktail 4 | VEGF | 5'-CCCUGGUGGACAUCUUCCAGGAGUA-3' | 12 |
| | EGFR | 5'-GAUCAUGGUCAAGUGCUGGAUGAUA-3' | 16 |
| | MMP-2 | 5'-CCCAAGUGGGACAAGAACCAGAUCA-3' | 249 |

TABLE 11

PDGF-EGFR-MGMT siRNA cocktails
siRNA Cocktail Combinations (siRNA sense sequences)

| PDGF EGFR MGMT | | Human and Mouse homologues | SEQ ID NO: |
|---|---|---|---|
| Cock-tail 1 | PDGF | 5'-GCCUGCUGCUCCUCGGCUGCGGAUA-3' | 5 |
| | EGFR | 5'-CCAUCGAUGUCUACAUGAUCAUGGU-3' | 14 |
| | MGMT | 5'-GCUGAAGGUUGUGAAAUUCGGAGAA-3' | 18 |
| Cock-tail 2 | PDGF | 5'-GCCUGCUGCUCCUCGGCUGCGGAUA-3' | 5 |
| | EGFR | 5'-CCAUCGAUGUCUACAUGAUCAUGGU-3' | 14 |
| | MGMT | 5'-GCUGCUGAAGGUUGUGAAAUUCGGA-3' | 20 |
| Cock-tail 3 | PDGF | 5'-GCCUGCUGCUCCUCGGCUGCGGAUA-3' | 5 |
| | EGFR | 5'-GAUCAUGGUCAAGUGCUGGAUGAUA-3' | 16 |
| | MGMT | 5'-GCUGCUGAAGGUUGUGAAAUUCGGA-3' | 20 |
| Cock-tail 4 | PDGF | 5'-GCCUGCUGCUCCUCGGCUGCGGAUA-3' | 5 |
| | EGFR | 5'-GAUCAUGGUCAAGUGCUGGAUGAUA-3' | 16 |
| | MGMT | 5'-GCUGAAGGUUGUGAAAUUCGGAGAA-3' | 18 |

TABLE 12

VEGF-EGFR-MGMT-other siRNA cocktails
siRNA Cocktail Combinations (siRNA sense sequences)

| VEGF EGFR MGMT | other | Human and Mouse homologues | SEQ ID NO: |
|---|---|---|---|
| Cock-tail 1 | VEGF | 5'-CUGUAGACACACCCACCCACAUACA-3' | 10 |
| | EGFR | 5'-CCAUCGAUGUCUACAUGAUCAUGGU-3' | 14 |
| | MGMT | 5'-GCUGAAGGUUGUGAAAUUCGGAGAA-3' | 18 |
| | PDGF | 5'-GCCUGCUGCUCCUCGGCUGCGGAUA-3' | 5 |
| Cock-tail 2 | VEGF | 5'-CUGUAGACACACCCACCCACAUACA-3' | 10 |
| | EGFR | 5'-CCAUCGAUGUCUACAUGAUCAUGGU-3' | 14 |
| | MGMT | 5'-GCUGCUGAAGGUUGUGAAAUUCGGA-3' | 20 |
| | MMP-2 | 5'-CCCAAGUGGGACAAGAACCAGAUCA-3' | 249 |
| Cock-tail 3 | VEGF | 5'-CUGUAGACACACCCACCCACAUACA-3' | 10 |
| | EGFR | 5'-GAUCAUGGUCAAGUGCUGGAUGAUA-3' | 16 |
| | MGMT | 5'-GCUGCUGAAGGUUGUGAAAUUCGGA-3' | 20 |
| | MMP-9 | 5'-CCAGUUUGGUGUCGCGGAGCACGGA-3' | 251 |
| Cock-tail 4 | VEGF | 5'-CCCUGGUGGACAUCUUCCAGGAGUA-3' | 12 |
| | MMP-2 | 5'-CCCAAGUGGGACAAGAACCAGAUCA-3' | 249 |
| | MGMT | 5'-GCUGCUGAAGGUUGUGAAAUUCGGA-3' | 20 |
| | MMP-9 | 5'-CCAGUUUGGUGUCGCGGAGCACGGA-3' | 251 |
| Cock-tail 5 | MMP-2 | 5'-CCCAAGUGGGACAAGAACCAGAUCA-3' | 249 |
| | EGFR | 5'-GAUCAUGGUCAAGUGCUGGAUGAUA-3' | 16 |
| | MGMT | 5'-GCUGAAGGUUGUGAAAUUCGGAGAA-3' | 18 |
| | PDGF | 5'-GCCUGCUGCUCCUCGGCUGCGGAUA-3' | 5 |

Experimental Design:

The design is summarized for three experiments that may be performed to evaluate the antitumorigenic effects of this method.

Experiment A.

To evaluate the antitumorigenic effects of the selected siRNAs individually and collectively in vitro as well as in vivo. The most potent siRNA inhibitors for each gene are transfected into established cell lines. Measuring cellular proliferation, apoptosis, and signaling pathways downstream of these genes serves as parameters for drug-target validation and potential siRNA-mediated antitumorigenesis in vivo. Then, all three siRNAs are transfected simultaneously into these cell lines to validate the biological potential of a combinatorial approach. This method is applied in vivo to GBM xenograft nude mice models. Evaluation of angiogenesis, proliferation, and apoptosis in these models is used to assess the efficacy of siRNA-mediated antitumorigenesis in vivo.

Experiment B.

To evaluate, both in vitro and in vivo, the antitumorigenic effects of using individual siRNA and a combination of the three siRNAs in conjunction with clinically available agents, including Tarceva (anti-EGFR), Avastin (anti-VEGF), and Temozolomide (TMZ). Each candidate siRNA, coupled with its clinically available agent, is transfected into established cell lines in vitro to assess the antitumorigenic potential of combined administration. For example, the most potent siRNA for EGFR can be delivered, along with Tarceva, to evaluate the combined effect of these two agents. Comparing proliferation, apoptosis, and downstream signaling activity in these trials to those conducted with siRNA only provides a means to evaluate the effects of combined treatment, as well as the potential for enhanced therapeutic vulnerability. After each siRNA-therapeutic agent pair has been evaluated individually in vitro, all three siRNAs, along with their existing therapeutic agents, are transfected into cell lines simultaneously. These trials are used as a proof of concept for achieving synergistic antitumorigenesis. Corresponding in vivo experiments are conducted using nude mouse models.

Experiment C.

To validate the efficacy of siRNA-mediated antitumorigenesis in vivo using a nanotechnology-based delivery system. Nanoparticle delivery of the siRNA and siRNA-therapeutic agent cocktails via local and systemic injection to the GBM mouse models is a means to validate multiple drug targets, as well as to indicate the potential therapeutic applications of siRNA. Moreover, the success of a systemic, nanoparticle delivery method in GBM animal models to effect antitumorigenesis serves to validate this approach for clinical trials.

Polymers Enhance siRNA Cocktail Delivery

As shown in a study using siRNA cocktails to inhibit ocular neovascularization induced by a herpes simplex viral sequence, the histidine-lysine (HK) polymer-siRNA nanoparticle-mediated local delivery has achieved potent anti-angiogenesis activity. In a separate study using HK polymer to enhance siRNA delivery intratumorally, the tumor growth curves showed significant anti-tumor efficacy with clear downregulation of the target gene expression. At 10 days after the injection of MDA-MB-435 cells into the mammary fat pad, mice with visible tumors were separated into treatment groups. Each group had four mice with eight tumors, and tumor size was assessed in two dimensions and calculated. Mice received 4 µg/tumor of siRNA with each intratumoral injection every 5 days. To confirm the antitumor efficacy of siRNA Raf-1 with the optimal polymer in greater detail, mice with tumors were divided into these groups: untreated, b-galactosidase siRNA, and Raf-1 siRNA. Clearly, HK polymer has been validated as an effective local siRNA delivery carrier.

Over the past few decades, biodegradable polyesters, such as poly(lactic acid) (PLA), poly(glycolic acid) (PGA), and poly(lactic-co-glycolic acid) (PLGA), have been extensively studied for a wide variety of pharmaceutical and biomedical applications. The biodegradable polyester family has been regarded as one of the few synthetic biodegradable polymers with controllable biodegradability, excellent biocompatibility, and high safety. The need for a variety of drug formulations for different drugs and delivery pathways resulted in development of various types of block copolymers (e.g., diblock, triblock, multiblock, and star-shaped block) consisting of the biodegradable polyesters and PEG.

PAMAM dendrimers represent an exciting new class of macromolecular architecture called "dense star" polymers. Unlike classical polymers, dendrimers have a high degree of molecular uniformity, narrow molecular weight distribution, specific size and shape characteristics, and a highly functionalized terminal surface. The manufacturing process is a series of repetitive steps starting with a central initiator core. Each subsequent growth step represents a new "generation" of polymer with a larger molecular diameter, twice the number of reactive surface sites, and approximately double the molecular weight of the preceding generation. PAMAM dendrimers are the most common class of dendrimers suitable for many materials science and biotechnology applications. PAMAM dendrimers consist of alkyl-diamine core and tertiary amine branches.

Cationic polymers have gained prominence in nonviral DNA delivery, although their use in siRNA delivery is much more recent. Of these polymers, PEI, which contains primary, secondary, and tertiary amines, has the unique abilities to complex nucleic acid and serve as a low pH (4-5) buffer. Owing to this buffering capacity or "proton sponge" effect, PEI has shown higher transfection efficiency than other cationic polymers. Recently, several groups have reported the use of PEI-siRNA complexes for the treatment of influenza in mice and systemic delivery for treatment of breast cancer in a mouse model, etc. However, in vivo toxicity has been noted for PEI upon intravenous administration. To reduce PEI toxicity, PEG was grafted onto PEI, greatly reducing toxicity for the resulting gene delivery complexes. The PEI component of the copolymer allows for complexation with polynucleotides, and it increases endosomal release of the nanocomplexes into the cytoplasm. The PEG component not only reduces toxicity of the PEI component, but also stabilizes the resulting nanocomplex. This modified vector was recently used to deliver siRNA targeting VEGF for treatment of angiogenic tumors. A copolymer composed of 10 PEG grafts (2 kDa each) per PEI polymer (2 k 10 copolymer) gave the highest binding affinity to siRNA by ethidium bromide exclusion assays, and it had the smallest nanocomplex size (115±13 nm diameter). When we tested this PEG-PEI-siRNA nanoparticle in mouse for pulmonary delivery, the anti-influenza A activity was very much enhanced, which allows us to achieve potent therapeutic effect. Therefore, this PEG-PEI could be used in our multi-targeted siRNA regimen for treatment of glioblastoma.

DOTAP Chloride has been used as DNA transfection reagent. Racemic DOTAP Chloride is a cationic lipid which forms liposomes in aqueous media, alone or in combination with other lipids. These liposomes can carry polar and nonpolar molecules (APIs or diagnostics). They can enter cells carrying their load through the cell membrane. We will use either R DOTAP Chloride or S DOTAP Chloride for siRNA cocktail delivery into the tumor tissue.

To test HK polymer, PLGA, and PAMAM for their role in enhancement of siRNA delivery in vivo, we need to define the formulations for each of these carrier-siRNA nanoparticles.

Ligands Useful for Targeted siRNA Delivery

The targeting ligands may also improve intracerebral or intratumoral siRNA delivery. The EGF receptor ligands, IL13 ligand, hepatocyte growth factor ligand, and other single chain monoclonal antibodies may be used for this type of targeting design.

RGD (arginine-glycine-aspartic acid) peptide ligands, such as the 'cyclic' 10mer RGD peptide with the sequence H-ACRGDMFGCA-OH (SEQ ID NO: 22), and -(D)CR(D)WKTCT-(ol) (SEQ ID NO: 253) have been used for neovasculature targeted nucleic acid delivery.

A short peptide derived from rabies virus glycoprotein (RVG) recently has been identified for its ability to enable the transvascular delivery of small interfering RNA (siRNA) (27). This 29-amino-acid peptide specifically binds to the acetylcholine receptor expressed by neuronal cells. To enable siRNA binding, a chimaeric peptide was synthesized by adding nonamer arginine residues at the carboxy terminus of RVG. This RVG-9R peptide was able to bind and transduce siRNA to neuronal cells in vitro and in vivo, resulting in efficient gene silencing. Peptides: RVG (YTIWMPENPRPGTPCDIFTNSRGKRASNG (SEQ ID NO: 23)), RVG-9R (YTIWMPENPRPGTPCDIFTNS-RGKRASNGGGGR-RRRRRRRR (SEQ ID NO: 254)).

REFERENCES

1. George D (2001) Platelet-derived growth factor receptors: a therapeutic target in solid tumors. Semin Oncol 28 (Suppl 17):27-33.
2. Abate-Shen C, Shen M M (2007) FGF signaling in prostate tumorigenesis—new insights into epithelial-stromal interactions. Cancer Cell 12 (6):495-7.
3. Yang F, Strand D W, Rowley D R (2008) Fibroblast growth factor-2 mediates transforming growth factor-beta action in prostate cancer reactive stroma. Oncogene 27 (4):450-9.
4. Hofer M D, Fecko A, Shen R, Setlur S R, Pienta K G, Tomlins S A, Chinnaiyan A M, Rubin M A (2004) Expression of the platelet-derived growth factor receptor in prostate cancer and treatment implications with tyrosine kinase inhibitors. Neoplasia 6 (5):503-12.
5. Shukla S, Maclennan G T, Hartman D J, Fu P, Resnick M I, Gupta S (2007) Activation of PI3K-Akt signaling pathway promotes prostate cancer cell invasion. Int J Cancer 121 (7):1424-32.
6. Manus M T, Sharp P A (2002) Gene silencing in mammals by small interfering RNAs. Nat Rev Genet 3 (10):737-47.
7. Lu P Y Xie F Y, Woodle M C (2003) siRNA-mediated antitumorigenesis for drug target validation and therapeutics. Curr Opin Mol Ther 5 (3):225-34.
8. Kim B Tang Q, Biswas P S, Xu J, Schiffelers R M, Xie F Y, Ansari A M, Scaria P V, Woodle M C, Lu P, Rouse B T (2004) Inhibition of ocular angiogenesis by siRNA targeting vascular endothelial growth factor-pathway genes; therapeutic strategy for herpetic stromal keratitis. Am J Pathol 165 (6): 2177-85.
9. Lu P Y, Woodle M C (2005) Delivering siRNA in vivo for functional genomics and novel therapeutics. In RNA Interference Technology, Appasani K, Ed. New York: Cambridge University Press, pp. 303-17.
10. Lu P Y, Xie F Y, Woodle M C (2005) Modulation of angiogenesis with siRNA inhibitors for novel therapeutics. Trends Mol Med 11 (3), 104-13.
11. Lu P Y, Xie F, Woodle M C (2005) In vivo application of RNA interference: from functional genomics to therapeutics. Adv Genet. 54:117-42.
12. Leng Q J, Mixson A J (2005) Small interfering RNA targeting Raf-1 inhibits tumor growth in vitro and in vivo. Cancer Gene Ther 12 (8):682-90.
13. Sutton D, Kim S, Shuai X, Leskov K, Marques J T, Williams B R, Boothman D A, Gao J (2006) Efficient suppression of secretory clusterin levels by polymer-siRNA nanocomplexes enhances ionizing radiation lethality in human MCF-7 breast cancer cells in vitro. Int J Nanomedicine 1 (2) 155-162.
14. Braun C S, Vetro J A, Tomalia D A, Koe G S, Koe J G, Middaugh C R. (2005) Structure/function relationships of polyamidoamine/DNA dendrimers as gene delivery vehicles. J Pharm Sci 94 (2), 423-36.
15. Woodle M C, Lu P Y (2005) Nanoparticles deliver RNAi therapy. Materials Today 8 (8), 34-41.
16. Xie Y F, Woodle M C, Lu P Y (2006) Harnessing in vivo siRNA delivery for drug discovery and therapeutic development. Drug Discov Today 11 (1-2):67-73.
17. Li B J, Tang Q, Cheng D, Qin C, Xie F Y, Wei Q, Xu J, Liu Y, Zheng B J, Woodle M C, Zhong N, Lu P Y (2005) Using siRNA in prophylactic and therapeutic regimens against SARS coronavirus in Rhesus macaque. Nat Med 11, 944-51.
18. Yan Z, Zou H, Tian F, Grandis J, Mixson A, Lu P, Li L (2008) Human rhomboid family-1 (RHBDF1) gene-silencing causes apoptosis or autophagy to epithelial cancer cells and inhibits xenograft tumor growth. Mol Cancer Ther, in press.
19. Leng Q, Scaria P, Lu P, Woodle M C, Mixson A J (2008) Systemic delivery of HK Raf-1 siRNA polyplexes inhibits MDA-MB-435 xenografts. Cancer Gene Ther, in press.
20. Oka N, Soeda A, Inagaki A, Onodera M, Maruyama H, Hara A, Kunisada T, Mori H, Iwama T (2007) VEGF promotes tumorigenesis and angiogenesis of human glioblastoma stem cells. Biochem Biophys Res Commun 360 (3): 553-9.
21. El-Obeid A, Bongcam-Rudloff E, Sörby M, Ostman A, Nistér M, Westermark B. (1997) Cell scattering and migration induced by autocrine transforming growth factor alpha in human glioma cells in vitro Cancer Res 57 (24):5598-604.
22. Nagane M, Coufal F, Lin H, Bögler O, Cavenee W K, Huang H J (1996) A common mutant epidermal growth factor receptor confers enhanced tumorigenicity on human glioblastoma cells by increasing proliferation and reducing apoptosis. Cancer Res 56 (21):5079-86.
23. Stommel J, Kimmelman A C, Ying H, Nabioullin R, Ponugoti A H, Wiedemeyer R, Stegh A H, Bradner J E, Ligon K L, Brennan C, Chin L, DePinho R A. (2007) Coactivation of receptor tyrosine kinases affects the response of tumor cells to targeted therapies Science 318: 287-90.
24. Huang P, Mukasa A, Bonavia R, Flynn R A, Brewer Z E, Cavenee W K, Furnari F B, White F M (2007) Quantitative analysis of EGFRvIII cellular signaling networks reveals a combinatorial therapeutic strategy for glioblastoma. Proc Natl Acad Sci USA 104 (31):12867-72.
25. Adjei A A (2006) Novel combinations based on epidermal growth factor receptor inhibition. Clin Cancer Res 12: 446-50 2006.
26. Reardon D A, Rich J N, Friedman H S, Bigner D D (2006) Recent advances in the treatment of malignant astrocytoma. J Clin Oncol 24:1253-65.
27. Kumar et al., "Transvascular delivery of small interfering RNA to the central nervous system," Nature doi:10.1038/nature-05901 (2007).
28. Carsten Culmsee; Edith Gasser, Sabine Hansen, Joerg-Christian TonnErnst Wagner and Roland Goldbrunner. Effects of Raf-1 siRNA on human cerebral microvascular endothelial cells: A potential therapeutic strategy for inhibition of tumor angiogenesis. Brain research. vol. 1125, pp. 147-154.
29. Friese M A, Wischhusen J, Wick W, Weiler M, Eisele G, Steinle A, Weller M. RNA interference targeting transforming growth factor-beta enhances NKG2D-mediated antiglioma immune response, inhibits glioma cell migration and invasiveness, and abrogates tumorigenicity in vivo. *Cancer Res.* 2004 Oct. 15; 64(20):7596-603.
30. Xiaoyi H u, Pier Paolo Pandolfi, Yi L i, Jason A Koutcher, Marc Rosenblum, and Eric C Holland. mTOR Promotes Survival and Astrocytic Characteristics Induced by Pten/Akt Signaling in Glioblastoma. Neoplasia. 2005 April; 7(4): 356-368.
31. Khong Bee Kang, Ting Ting Wang, Chow Thai Woon, Elizabeth S. Cheah, F. R. C. Path†, Xiao Lei Moore, Congju Zhu, Meng Cheong Wong, F.R.C.P. Enhancement of glioblastoma radioresponse by a selective COX-2 inhibitor celecoxib: Inhibition of tumor angiogenesis with extensive tumor necrosis. Radiation Oncology, 67(3) 3888-896.

All publications, including issued patents and published applications, and all database entries identified by url addresses or accession numbers are incorporated herein by reference in their entirety.

Although this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

---

What is claimed is:

1. A composition comprising at least three isolated siRNA molecules, wherein at least one isolated siRNA molecule (sense: 5'-CUGUAGACACACCCACCCACAUACA-3' (SEQ ID NO: 10), antisense: 5'-UGUAUGUGGGUGGGU-GUGUCUACAG-3') (SEQ ID NO: 11) binds to an mRNA molecule that encodes a human VEGF protein and binds to an mRNA molecule that encodes a mouse VEGF protein, at least one isolated siRNA molecule (sense: 5'-CCAUCGAUGUC-UACAUGAUCAUGGU-3' (SEQ ID NO: 14), antisense: 5'-ACCAUGAUCAUGUAGACAUCGAUGG-3') (SEQ ID NO: 15) binds to an mRNA molecule that encodes a human EGFR protein and binds to an mRNA molecule that encodes a mouse EGFR protein, and at least one isolated siRNA molecule (sense: 5'-GCUGAAGGUUGUGAAAUUCG-GAGAA-3' (SEQ ID NO: 18), antisense: 5'-UUCUC-CGAAUUUCACAACCUUCAGC-3') (SEQ ID NO: 19) binds to an mRNA molecule that encodes a human MGMT protein and binds to an mRNA molecule that encodes a mouse MGMT protein.

2. The composition of claim 1, further comprising a pharmaceutically acceptable carrier.

3. The composition of claim 2, wherein said carrier comprises at least one of the following: a glucose solution, a polycationic binding agent, a cationic lipid, a cationic micelle, a cationic polypeptide, a hydrophilic polymer grafted polymer, a non-natural cationic polymer, a cationic polyacetal, a hydrophilic polymer grafted polyacetal, a ligand functionalized cationic polymer, a ligand functionalized-hydrophilic polymer grafted polymer, and a ligand functionalized liposome.

4. The composition of claim 3, wherein said ligand comprises one or more of an RGD peptide, an RVG peptide, or a FROP peptide.

5. The composition of claim 3, wherein said polymers comprise a biodegradable histidine-lysine polymer, a biodegradable polyester, a polyamidoamine (PAMAM) dendrimer, a cationic lipid, optionally DOTAP, and a PEGylated PEI.

6. The composition of claim 2, wherein said carrier comprises a histidine-lysine copolymer that forms a nanoparticle with the siRNA molecules.

7. The composition of claim 1, further comprising a therapeutic agent that impedes or blocks tumorigenesis, angiogenesis, or cell proliferation in the brain or spinal cord of a mammal.

8. The composition of claim 7, wherein said therapeutic agent is selected from the group consisting of bevacizumab, sunitinib, sorafenib, temsirolimus, and temozolomide.

9. A nanoparticle comprising the siRNA molecules of claim 1, a pharmaceutically acceptable carrier, and a targeting ligand.

10. The nanoparticle of claim 9, wherein said pharmaceutically accepable carrier is a histidine-lysine copolymer.

11. The nanoparticle of claim 9, wherein said targeting ligand is selected from the group consisting of EGF receptor ligands, IL13 ligand, hepatocyte growth factor ligand, single chain monoclonal antibodies, RGD peptide ligands, and RVG peptide ligands.

12. The composition of claim 4 wherein said RGD peptide is H-ACRGDMFGCA-OH, said RVG peptide is H-YTIW-MPENPRPGTPCDIFTNSRGKRASNG-OH, and said FROP peptide is H-EDYELMDLLAYL-OH.

13. The composition of claim 5 wherein said biodegradable polyester comprises poly(lactic acid) (PLA), poly(glycolic acid) (PGA), or poly(lactic-co-glycolic acid) (PLGA).

14. The nanoparticle of claim 9 wherein said targeting ligand is an RGD peptide ligand or an RVG peptide ligand.

15. The nanoparticle of claim 14 wherein said RGD peptide ligand is a 'cyclic' 10mer RGD peptide with the sequence H-ACRGDMFGCA-OH, and -(D)CR(D)WKTCT-(ol).

16. The nanoparticle of claim 14 wherein said RVG peptide ligand is YTIWMPENPRPGTPCDIFTNSRGKRASNG or YTIWMPENPRPGTPCDIFTNS-RGKRASNGGGGR-RRRRRRRR.

* * * * *